United States Patent
Azuma et al.

(10) Patent No.: US 6,649,625 B2
(45) Date of Patent: Nov. 18, 2003

(54) AGENT FOR PROPHYLAXIS AND TREATMENT OF GLAUCOMA

(75) Inventors: Mitsuyoshi Azuma, Nishinomiya (JP); Yukuo Yoshida, Kobe (JP); Mitsunori Waki, Kobe (JP); Masayoshi Uehata, Hirakata (JP)

(73) Assignees: Senju Pharmaceutical Co., Ltd., Osaka (JP); Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 10/298,674

(22) Filed: Nov. 19, 2002

(65) Prior Publication Data

US 2003/0125351 A1 Jul. 3, 2003

Related U.S. Application Data

(62) Division of application No. 09/529,354, filed as application No. PCT/JP99/04403 on Aug. 13, 1999.

(30) Foreign Application Priority Data

Aug. 17, 1998 (JP) .......................................... 10-247762
Apr. 28, 1999 (JP) .......................................... 11-122960

(51) Int. Cl.$^7$ .............................................. A61K 31/44
(52) U.S. Cl. ........................ 514/303; 514/300; 514/912
(58) Field of Search ................................. 514/300, 303, 514/912

(56) References Cited

U.S. PATENT DOCUMENTS

| | | | |
|---|---|---|---|
| 4,838,677 A | 6/1989 | Bronskill et al. | |
| 5,478,838 A | 12/1995 | Arita et al. | 514/300 |
| 5,618,955 A | 4/1997 | Mechoulam et al. | 554/66 |
| 5,888,173 A | 3/1999 | Singhal | |
| 5,906,819 A | 5/1999 | Kaibuchi et al. | 424/94.5 |
| 5,958,944 A | 9/1999 | Arita et al. | 514/300 |

FOREIGN PATENT DOCUMENTS

| | | |
|---|---|---|
| EP | 0 956 865 | 11/1999 |
| JP | 5-213940 | 8/1993 |
| JP | 7-504099 | 5/1995 |
| JP | 8-504195 | 5/1996 |
| JP | 8-198876 | 8/1996 |
| JP | 10-113187 | 5/1998 |
| WO | 93/15732 | 8/1993 |
| WO | 97/23222 | 7/1997 |
| WO | 97/30701 | 8/1997 |
| WO | 98/06433 | 2/1998 |

OTHER PUBLICATIONS

PDR 29 Edition 2001 ALCON/219 ISOPTO Carbachol, Adverse Reactions, "The premier source of definitive medical information", 2000, published by Medical Economics Company, Inc. at Montvale, NJ.
Bulletin of the Osaka Medical School 13, 42–51 (1967) "Group Therapy with Tropic Acid Amide (Mydrin M) against Pseudo–Myopia in Primary School Children", Yamaji et al., pp. 42–51.
Investigative Ophthalmology & Visual Science, 26, 1024–1028 (1985), Gilmartin et al., The relationship between Tonic Accommodation and Ciliary Muscle Innervation, vol. 26, pp. 1024–1028.
WPI English Abstract of JP 8–198876 A.
WPI English Abstract of JP 3–218356 A (Sep. 1991).
WPI English Abstract of JP 62–89679 A (Apr. 1987).
WPI English Abstract of JP 4–273821 A (Sep. 1992).
Masayoshi Uehata et al., "Calcium Sensitization of Smooth Muscle Mediated by a Rho–Associated Protein Kinase in Hypertension", Nature, vol. 389, Oct. 30, 1997, pp. 990–994.

*Primary Examiner*—Zohreh Fay
(74) *Attorney, Agent, or Firm*—Wenderoth, Lind & Ponack, L.L.P.

(57) ABSTRACT

An agent for the prophylaxis and treatment of glaucoma, which contains a compound having a Rho kinase inhibitory activity, particularly an agent for the prophylaxis and treatment of glaucoma, which contains a compound of the formula (I)

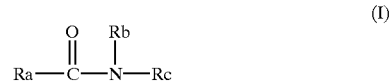

(I)

wherein each symbol is as defined in the specification, as the compound having a Rho kinase inhibitory activity, is provided. The agent for the prophylaxis and treatment of glaucoma of the present invention is a novel agent for the prophylaxis and treatment of glaucoma and has intraocular pressure lowering action, optic disc blood flow improving action and aqueous humor outflow promoting action.

9 Claims, 7 Drawing Sheets

AGENT FOR PROPHYLAXIS AND TREATMENT OF GLAUCOMA

This is a divisional of Ser. No. 09/529,354, filed Apr. 13, 2000 which is a 371 of PCT/JP99/04403 filed Aug. 13, 1999.

TECHNICAL FIELD

The present invention relates to an agent for the prophylaxis and treatment of glaucoma. More specifically, the present invention relates to an agent for the prophylaxis and treatment of glaucoma, which comprises a compound having a Rho kinase inhibitory activity as an active ingredient.

BACKGROUND ART

Glaucoma is caused by an abnormally high internal pressure of the eyeball, wherein the abnormally high pressure makes the eye grow dim or hurts the eye, which in turn fails the eyesight little by little possibly into blindness. Normally, an aqueous humor continuously circulates in the eyeball and maintains a constant intraocular pressure (10–20 mmHg). The pressure is maintained by the circulation of the blood and lymphocytes, elasticity of the eyeball wall, the performance of the control nerves and the like. An abnormality in any of them results in a rise of the intraocular pressure, which may develop glaucoma.

With the aim of preventing the intraocular pressure from rising or lowering an intraocular pressure that went up, for the prophylaxis and treatment of glaucoma, various drugs have been used. Known eye drops for the therapy of glaucoma include sympathetic agonists such as epinephrine, dipivefrine and the like. Due to mydriatic action, however, these eye drops enhance angle closure when administered to treat narrow angle glaucoma, and may cause not only an acute rise of the intraocular pressure, but also hypertension and pigmentation deposit. In addition, the parasympathetic agonists such as pilocarpine and the like cause side effects such as dark visual field due to miosis and congested eye, iris cyst, posterior synechia, cataract, retinal detachment and the like after a long-term use. Moreover, β-adrenalin blockers such as timolol, pindolol and the like have been widely used, because they lower intraocular pressure by inhibiting the production of aqueous humor without acting on pupils. However, their use is limited, because β-adrenalin blockers have been reported to cause side effects such as local dry feeling of the eye, allergic blepharitis, superficial keratitis and the like, as well as systemic side effects such as bradycardia, heart failure, asthmatic fit and the like. These side effects prevent application of the blockers to patients suffering from such symptoms. A recent suggestion of an aqueous humor outflow promoting effect of α1-adrenalin blockers also suggests potential use of bunazosin hydrochloride and the like as a new therapeutic agent of glaucoma (Ikuo Azuma, Folia Ophthalmol. Jpn.,42,710–714,1991). However, the α1-adrenalin blockers are inevitably associated with conjunctival injection and miosis due to their vasodilating action.

In the meantime, a compound having a Rho kinase inhibitory activity has been reported to show a hypotensive effect on various hypertension model animals (Masayoshi Uehata, et al., Nature 389, 990–994, 1997). The Rho kinase has been confirmed to be present in corneal epithelial cells (Nirmala SundarRaj. et al., IOVS, 39(7) 1266–1272, 1998). However, it is unknown if Rho kinase is present in other ophthalmic tissues.

The pharmaceutical use of the compound having a Rho kinase inhibitory activity is disclosed in WO98/06433, and, as a use in the ophthalmic area, is taught to be useful for retinopathy. However, WO98/06433 does not disclose its usefulness against glaucoma or description suggestive of the effect.

As a compound having a Rho kinase inhibitory activity, a compound of formula (I) to be mentioned later has been reported (WO98/06433). The compound of formula (I) has been already known to be useful as an agent for the prophylaxis and treatment of disorders of circulatory organs such as coronary, cerebral, renal, peripheral artery and the like (e.g., a therapeutic agent of hypertension, a therapeutic agent of angina pectoris, a therapeutic agent of renal and peripheral circulation disorder, a suppressive agent of cerebrovascular contraction and the like), which is potent and long lasting, and also as a therapeutic agent of asthma (JP-A-62-89679, JP-A-3-218356, JP-A-4-273821, JP-A-5-194401, JP-A-6-41080 and WO95/28387).

However, these compounds of the formula (I) are not disclosed to be useful for glaucoma, and there is no description suggestive of such usefulness.

DISCLOSURE OF THE INVENTION

The present invention aims at solving the above-mentioned problems and provides a novel agent for the prophylaxis and treatment of glaucoma, which is superior in a prophylactic and therapeutic effect on glaucoma.

The present inventors have conducted intensive studies and found that a compound having a Rho kinase inhibitory activity also has an intraocular pressure lowering action, an optic disc blood flow improving action and an aqueous outflow promoting action, and that it is useful for the prophylaxis and treatment of various types of glaucoma, which resulted in the completion of the present invention.

Accordingly, the present invention provides the following.

(1) An agent for the prophylaxis and treatment of glaucoma, which comprises a compound having a Rho kinase inhibitory activity.

(2) The agent for the prophylaxis and treatment of glaucoma of (1) above, wherein the compound having a Rho kinase inhibitory activity is an amide compound of the following formula (I)

wherein

Ra is a group of the formula

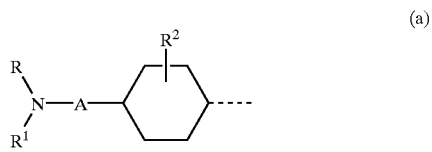

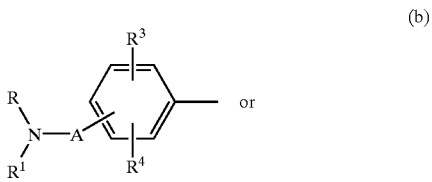

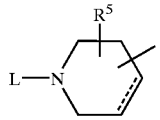

in the formulas (a) and (b),

R is hydrogen, alkyl, or cycloalkyl, cycloalkylalkyl, phenyl or aralkyl, which optionally has a substituent on the ring, or a group of the formula

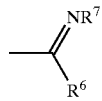

wherein $R^6$ is hydrogen, alkyl or formula: $—NR^8NR^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally having, in the ring, oxygen atom, sulfur atom or optionally substituted nitrogen atom, $R^1$ is hydrogen, alkyl, or cycloalkyl, cycloalkylalkyl, phenyl or aralkyl, which optionally has a substituent on the ring, or R and $R^1$ in combination form, together with the adjacent nitrogen atom, a group forming a heterocycle optionally having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, alkylcarbamoyl or azide, and A is a group of the formula

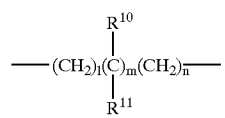

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, in the formula (c), L is hydrogen, alkyl, aminoalkyl, mono- or dialkylaminoalkyl, tetrahydrofurfuryl, carbamoylalkyl, phthalimidoalkyl, amidino or a group of the formula

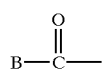

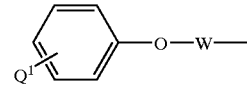

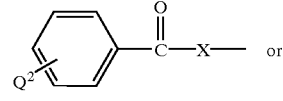

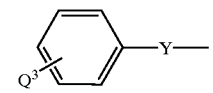

wherein B is hydrogen, alkyl, alkoxy, aralkyl, aralkyloxy, aminoalkyl, hydroxyalkyl, alkanoyloxyalkyl, alkoxycarbonylalkyl, α-aminobenzyl, furyl, pyridyl, phenyl, phenylamino, styryl or imidazopyridyl, $Q^1$ is hydrogen, halogen, hydroxy, aralkyloxy or thienylmethyl, W is alkylene, $Q^2$ is hydrogen, halogen, hydroxy or aralkyloxy, X is alkylene, $Q^3$ is hydrogen, halogen, hydroxy, alkoxy, nitro, amino, 2,3-dihydrofuryl or 5-methyl-3-oxo-2,3,4,5-tetrahydropyridazin-6-yl;

and Y is a single bond, alkylene or alkenylene, and in the formula (c), a broken line is a single bond or a double bond, and $R^5$ is hydrogen, hydroxy, alkoxy, alkoxycarbonyloxy, alkanoyloxy or aralkyloxycarbonyloxy;

Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

(3) The agent for the prophylaxis and treatment of glaucoma of (1) or (2) above, wherein the compound having a Rho kinase inhibitory activity is an amide compound of the following formula (I')

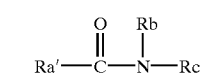

wherein

Ra' is a group of the formula

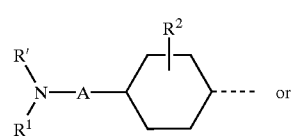

-continued

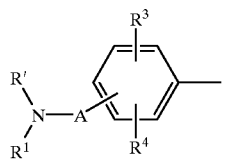

(b')

wherein
R' is hydrogen, alkyl, or cycloalkyl, cycloalkylalkyl, phenyl or aralkyl, which optionally has a substituent on the ring,
$R^1$ is hydrogen, alkyl, or cycloalkyl, cycloalkylalkyl, phenyl or aralkyl, which optionally has a substituent on the ring, or R' and $R^1$ in combination form, together with the adjacent nitrogen atom, a group forming a heterocycle optionally having, in the ring, oxygen atom, sulfur atom or optionally substituted nitrogen atom,
$R^2$ is hydrogen or alkyl,
$R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, alkylcarbamoyl or azide, and
A is a group of the formula

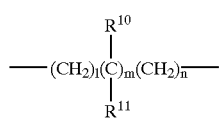

(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3,
Rb is a hydrogen, an alkyl, an aralkyl, an aminoalkyl or a mono- or dialkylaminoalkyl; and
Rc is an optionally substituted heterocycle containing nitrogen,
an isomer thereof and/or a pharmaceutically acceptable acid addition salt thereof.
(4) The agent for the prophylaxis and treatment of glaucoma of (1) above, wherein the compound having a Rho kinase inhibitory activity is (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide, (R)-(+)-N-(1H-pyrrolo[2,3-b]pyridin-4-yl)-4-(1-aminoethyl)benzamide and/or a pharmaceutically acceptable acid addition salt thereof.
(5) The agent for the prophylaxis and treatment of glaucoma of (1) above, which is administered to a local site in the eye.
(6) The agent for the prophylaxis and treatment of glaucoma of (5) above, which is in the form of an eye drop.
(7) A pharmaceutical composition for the prophylaxis and treatment of glaucoma, which comprises a compound having a Rho kinase inhibitory activity and a pharmaceutically acceptable carrier.
(8) The pharmaceutical composition for the prophylaxis and treatment of glaucoma of (7) above, wherein the compound having a Rho kinase inhibitory activity is an amide compound of the following formula (I)

(I)

wherein each symbol is as defined above, an isomer thereof and/or a pharmaceutically acceptable acid addition salt thereof.
(9) The pharmaceutical composition for the prophylaxis and treatment of glaucoma of (7) or (8) above, wherein the compound having a Rho kinase inhibitory activity is an amide compound of the following formula (I')

(I')

wherein each symbol is as defined above, an isomer thereof and/or a pharmaceutically acceptable acid addition salt thereof.
(10) The pharmaceutical composition for the prophylaxis and treatment of glaucoma of (7) above, wherein the compound having a Rho kinase inhibitory activity is (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide, (R)-(+)-N-(1H-pyrrolo[2,3-b]pyridin-4-yl)-4-(1-aminoethyl)benzamide and/or a pharmaceutically acceptable acid addition salt thereof.
(11) The pharmaceutical composition for the prophylaxis and treatment of glaucoma of (7) above, which is for administration to local site in the eye.
(12) The pharmaceutical composition for the prophylaxis and treatment of glaucoma of (11) above, which is in the form of an eye drop.
(13) A method of the prophylaxis and treatment of glaucoma, which comprises administering an effective amount of a compound having a Rho kinase inhibitory activity to a patient.
(14) The method of the prophylaxis and treatment of glaucoma of (13) above, wherein the compound having a Rho kinase inhibitory activity is an amide compound of the following formula (I)

(I)

wherein each symbol is as defined above, an isomer thereof and/or a pharmaceutically acceptable acid addition salt thereof.
(15) The method of the prophylaxis and treatment of glaucoma of (13) or (14) above, wherein the compound having a Rho kinase inhibitory activity is an amide compound of the following formula (I')

(I')

wherein each symbol is as defined above, an isomer thereof and/or a pharmaceutically acceptable acid addition salt thereof.

(16) The method of the prophylaxis and treatment of glaucoma of (13) above, wherein the compound having a Rho kinase inhibitory activity is (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide, (R)-(+)-N-(1H-pyrrolo[2,3-b]pyridin-4-yl)-4-(1-aminoethyl)benzamide and/or a pharmaceutically acceptable acid addition salt thereof.

(17) The method of the prophylaxis and treatment of glaucoma of (13) above, wherein the administration to a patient is that to a local site in the eye.

(18) The method of the prophylaxis and treatment of glaucoma of (17) above, wherein the administration to a patient is by instillation.

(19) Use of a compound having a Rho kinase inhibitory activity for the production of an agent for the prophylaxis and treatment of glaucoma.

(20) The use of (19) above, wherein the compound having a Rho kinase inhibitory activity is an amide compound of the following formula (I)

wherein each symbol is as defined above, an isomer thereof and/or a pharmaceutically acceptable acid addition salt thereof.

(21) The use of (19) or (20) above, wherein the compound having a Rho kinase is an amide compound of the following formula (I')

wherein each symbol is as defined above, an isomer thereof and/or a pharmaceutically acceptable acid addition salt thereof.

(22) The use of (19) above, wherein the compound having a Rho kinase inhibitory activity is (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide, (R)-(+)-N-(1H-pyrrolo[2,3-b]pyridin-4-yl)-4-(1-aminoethyl)benzamide and/or a pharmaceutically acceptable acid addition salt thereof.

(23) The use of (19) above, wherein the agent for the prophylaxis and treatment of glaucoma is for administration to a local site in the eye.

(24) The use of (23) above, wherein the agent for the prophylaxis and treatment of glaucoma is in the form of an eye drop.

(25) A commercial package comprising a pharmaceutical composition for the prophylaxis and treatment of glaucoma of any of (7) to (12) above, and a written matter associated therewith, the written matter stating that the pharmaceutical composition can or should be used for the prophylaxis and treatment of glaucoma.

DETAILED DESCRIPTION OF THE INVENTION

Figure 1:
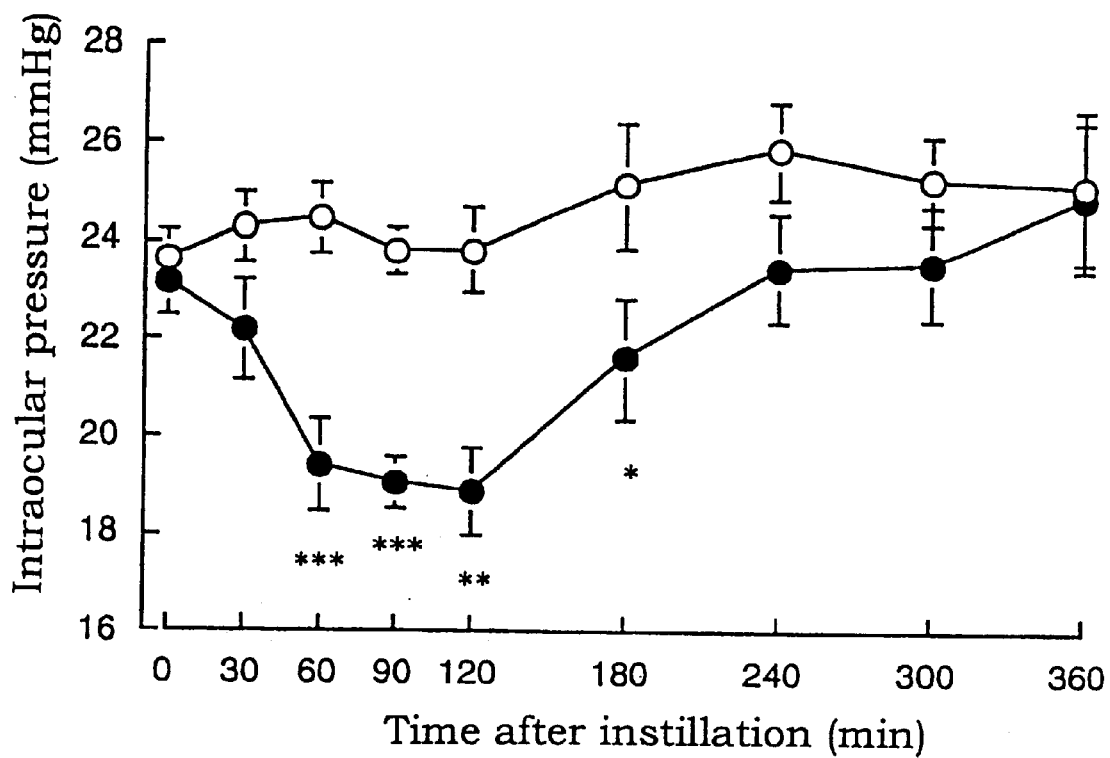
FIG. 1 is a graph showing the effect of the eye drop of Example 1 on the normal intraocular pressure, wherein the ordinate shows intraocular pressure, the abscissa shows time after instillation, ● shows the eye instilled with the eye drop of Example 1 and ○ shows control eye (n=6, *p<0.05, p<0.01, *p<0.001).

In the present invention, glaucoma is exemplified by primary open angle glaucoma, normal pressure glaucoma, hypersecretion glaucoma, ocular hypertension, acute angle closure glaucoma, chronic angle closer glaucoma, plateau iris syndrome, combined-mechanism glaucoma, steroid glaucoma, capsular glaucoma, pigmentary glaucoma, secondary glaucoma associated with amyloidosis, neovascular glaucoma, malignant glaucoma and the like.

In the present invention, Rho kinase means serine/threonine kinase activated along with the activation of Rho. For example, ROKα (ROCKII:Leung, T. et al, J. Biol. Chem., 270, 29051–29054, 1995), p160 ROCK (ROKβ, ROCK-I: Ishizaki, T. et al, The EMBO J., 15(8), 1885–1893, 1996) and other proteins having a serine/threonine kinase activity are exemplified.

The compound having a Rho kinase inhibitory activity used as an active ingredient in the present invention may be any as long as it has a Rho kinase inhibitory activity. For example, the compounds of the formula (I) are exemplified. Of these, a compound of the formula (I') is more preferably used. In the present invention, a compound having one kind of Rho kinase inhibitory activity can be used alone or, where necessary, several kinds of the compounds can be used.

In the present specification, each symbol of the formulas (I) and (I') is defined as follows.

Alkyl at R, R' and $R^1$ is linear or branched alkyl having 1 to 10 carbon atoms, which is exemplified by methyl, ethyl, propyl, isopropyl, butyl, isobutyl, sec-butyl, tert-butyl, pentyl, hexyl, heptyl, octyl, nonyl, decyl and the like, with preference given to alkyl having 1 to 4 carbon atoms.

Cycloalkyl at R, R' and $R^1$ has 3 to 7 carbon atoms and is exemplified by cyclopropyl, cyclobutyl, cyclopentyl, cyclohexyl, cycloheptyl and the like.

Cycloalkylalkyl at R, R' and $R^1$ is that wherein the cycloalkyl moiety is the above-mentioned cycloalkyl having 3 to 7 carbon atoms and the alkyl moiety is linear or branched alkyl having 1 to 6 carbon atoms (e.g., methyl, ethyl, propyl, isopropyl, butyl, pentyl, hexyl and the like), which is exemplified by cyclopropylmethyl, cyclobutylmethyl, cyclopentylmethyl, cyclohexylmethyl, cycloheptylmethyl, cyclopropylethyl, cyclopentylethyl, cyclohexylethyl, cycloheptylethyl, cyclopropylpropyl, cyclopentylpropyl, cyclohexylpropyl, cycloheptylpropyl, cyclopropylbutyl, cyclopentylbutyl, cyclohexylbutyl, cycloheptylbutyl, cyclopropylhexyl, cyclopentylhexyl, cyclohexylhexyl, cycloheptylhexyl and the like.

Aralkyl at R, R' and $R^1$ is that wherein alkyl moiety is alkyl having 1 to 4 carbon atoms and is exemplified by phenylalkyl such as benzyl, 1-phenylethyl, 2-phenylethyl, 3-phenylpropyl, 4-phenylbutyl and the like.

The substituent of optionally substituted cycloalkyl, cycloalkylalkyl, phenyl and aralkyl on the ring at R, R' and $R^1$ is halogen (e.g., chlorine, bromine, fluorine and iodine), alkyl (same as alkyl at R, R' and $R^1$), alkoxy (linear or branched alkoxy having 1 to 6 carbon atoms, such as methoxy, ethoxy, propoxy, isopropoxy, butoxy, isobutoxy, sec-butoxy, tert-butoxy, pentyloxy, hexyloxy and the like), aralkyl (same as aralkyl at R, R' and $R^1$) or haloalkyl (alkyl at R, R' and $R^1$ which is substituted by 1–5 halogen, and exemplified by fluoromethyl, difluoromethyl, trifluoromethyl, 2,2,2-trifluoroethyl, 2,2,3,3,3-pentafluoropropyl and the like), nitro, amino, cyano, azide and the like.

The group formed by R and R' or R' and $R^1$ in combination together with the adjacent nitrogen atom, which forms a heterocycle optionally having, in the ring, oxygen atom, sulfur atom or optionally substituted nitrogen atom is preferably a 5 or 6-membered ring and bonded ring thereof. Examples thereof include 1-pyrrolidinyl, piperidino, 1-piperazinyl, morpholino, thiomorpholino, 1-imidazolyl, 2,3-dihydrothiazol-3-yl and the like. The substituent of the optionally substituted nitrogen atom is exemplified by alkyl, aralkyl, haloalkyl and the like. As used herein, alkyl, aralkyl and haloalkyl are as defined for R, R' and $R^1$.

Alkyl at $R^2$ is as defined for R, R' and $R^1$.

Halogen, alkyl, alkoxy and aralkyl at $R^3$ and $R^4$ are as defined for R, R' and $R^1$.

Acyl at $R^3$ and $R^4$ is alkanoyl having 2 to 6 carbon atoms (e.g., acetyl, propionyl, butyryl, valeryl, pivaloyl and the like), benzoyl or phenylalkanoyl wherein the alkanoyl moiety has 2 to 4 carbon atoms (e.g., phenylacetyl, phenylpropionyl, phenylbutyryl and the like).

Alkylamino at $R^3$ and $R^4$ is that wherein the alkyl moiety is alkylamino having linear or branched alkyl having 1 to 6 carbon atoms. Examples thereof include methylamino, ethylamino, propylamino, isopropylamino, butylamino, isobutylamino, sec-butylamino, tert-butylamino, pentylamino, hexylamino and the like.

Acylamino at $R^3$ and $R^4$ is that wherein acyl moiety is alkanoyl having 2 to 6 carbon atoms, benzyl or the alkanoyl moiety is phenylalkanoyl having 2 to 4 carbon atoms and the like, which is exemplified by acetylamino, propionylamino, butyrylamino, valerylamino, pivaloylamino, benzoylamino, phenylacetylamino, phenylpropionylamino, phenylbutyrylamino and the like.

Alkylthio at $R^3$ and $R^4$ is that wherein the alkyl moiety is linear or branched alkyl having 1 to 6 carbon atoms, which is exemplified by methylthio, ethylthio, propylthio, isopropylthio, butylthio, isobutylthio, sec-butylthio, tert-butylthio, pentylthio, hexylthio and the like.

Aralkyloxy at $R^3$ and $R^4$ is that wherein the alkyl moiety is alkyl having 1 to 4 carbon atoms, which is exemplified by benzyloxy, 1-phenylethyloxy, 2-phenylethyloxy, 3-phenylpropyloxy, 4-phenylbutyloxy and the like.

Aralkylthio at $R^3$ and $R^4$ is that wherein the alkyl moiety is alkyl having 1 to 4 carbon atoms, which is exemplified by benzylthio, 1-phenylethylthio, 2-phenylethylthio, 3-phenylpropylthio, 4-phenylbutylthio and the like.

Alkoxycarbonyl at $R^3$ and $R^4$ is that wherein the alkoxy moiety is linear or branched alkoxy having 1 to 6 carbon atoms, which is exemplified by methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like.

Alkylcarbamoyl at $R^3$ and $R^4$ is carbamoyl mono- or di-substituted by alkyl having 1 to 4 carbon atoms, which is exemplified by methylcarbamoyl, dimethylcarbamoyl, ethylcarbamoyl, diethylcarbamoyl, propylcarbamoyl, dipropylcarbamoyl, butylcarbamoyl, dibutylcarbamoyl and the like.

Alkoxy at $R^5$ is as defined for R, R' and $R^1$.

Alkoxycarbonyloxy at $R^5$ is that wherein the alkoxy moiety is linear or branched alkoxy having 1 to 6 carbon atoms, which is exemplified by methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, tert-butoxycarbonyloxy, pentyloxycarbonyloxy, hexyloxycarbonyloxy and the like.

Alkanoyloxy at $R^5$ is that wherein the alkanoyl moiety is alkanoyl having 2 to 6 carbon atoms, which is exemplified by acetyloxy, propionyloxy, butyryloxy, valeryloxy, pivaloyloxy and the like.

Aralkyloxycarbonyloxy at $R^5$ is that wherein the aralkyl moiety is aralkyl having $C_1$–$C_4$ alkyl, which is exemplified by benzyloxycarbonyloxy, 1-phenylethyloxycarbonyloxy, 2-phenylethyloxycarbonyloxy, 3-phenylpropyl-oxycarbonyloxy, 4-phenylbutyloxycarbonyloxy and the like.

Alkyl at $R^6$ is as defined for R, R' and $R^1$; alkyl at $R^8$ and $R^9$ is as defined for R, R' and $R^1$; and aralkyl at $R^8$ and $R^9$ is as defined for R, R' and $R^1$.

Alkyl at $R^7$ is as defined for R, R' and $R^1$ and aralkyl at $R^7$ is as defined for R, R' and $R^1$.

The group formed by $R^6$ and $R^7$ in combination, which forms a heterocycle optionally having, in the ring, oxygen atom, sulfur atom or optionally substituted nitrogen atom, is imidazol-2-yl, thiazol-2-yl, oxazol-2-yl, imidazolin-2-yl, 3,4,5,6-tetrahydropyridin-2-yl, 3,4,5,6-tetrahydropyrimidin-2-yl, 1,3-oxazolin-2-yl, 1,3-thiazolin-2-yl or optionally substituted benzoimidazol-2-yl, benzothiazol-2-yl, benzoxazol-2-yl and the like having a substituent such as halogen, alkyl, alkoxy, haloalkyl, nitro, amino, phenyl, aralkyl and the like. As used herein, halogen, alkyl, alkoxy, haloalkyl and aralkyl are as defined for R, R' and $R^1$.

The substituent of the above-mentioned optionally substituted nitrogen atom is exemplified by alkyl, aralkyl, haloalkyl and the like. As used herein, alkyl, aralkyl and haloalkyl are as defined for R, R' and $R^1$.

Hydroxyalkyl at $R^{10}$ and $R^{11}$ is linear or branched alkyl having 1 to 6 carbon atoms which is substituted by 1 to 3 hydroxy, which is exemplified by hydroxymethyl, 2-hydroxyethyl, 1-hydroxyethyl, 3-hydroxypropyl, 4-hydroxybutyl and the like. Alkyl at $R^{10}$ and $R^{11}$ is as defined for R, R' and $R^1$; haloalkyl and alkoxycarbonyl at $R^{10}$ and $R^{11}$ are as defined for R, R' and $R^1$; aralkyl at $R^{10}$ and $R^{11}$ is as defined for R, R' and $R^1$; and cycloalkyl formed by $R^{10}$ and $R^{11}$ in combination is the same as cycloalkyl at R, R' and $R^1$.

Alkyl at L is as defined for R, R' and $R^1$.

Aminoalky at L is a linear or branched alkyl having 1 to 6 carbon atoms, which is substituted by amino, which is exemplified by aminomethyl, 2-aminoethyl, 1-aminoethyl, 3-aminopropyl, 4-aminobutyl, 5-aminopentyl, 6-aminohexyl and the like.

Mono- or dialkylaminoalkyl at L is mono- or di-substituted aminoalkyl with alkyl having 1 to 4 carbon atoms, which is exemplified by methylaminomethyl, dimethylaminomethyl, ethylaminomethyl, diethylaminomethyl, propylaminomethyl, dipropylaminomethyl, butylaminomethyl, dibutylaminomethyl, 2-dimethylaminoethyl, 2-diethylaminoethyl and the like.

Carbamoylalkyl at L is linear or branched alkyl having 1 to 6 carbon atoms substituted by carbamoyl, which is exemplified by carbamoylmethyl, 2-carbamoylethyl, 1-carbamoylethyl, 3-carbamoylpropyl, 4-carbamoylbutyl, 5-carbamoylpentyl, 6-carbamoylhexyl and the like.

Phthalimidoalkyl at L is linear or branched alkyl having 1 to 6 carbon atoms, which is substituted by phthalimide. Examples thereof include phthalimidomethyl, 2-phthalimidoethyl, 1-phthalimidoethyl, 3-phthalimidopropyl, 4-phthalimidobutyl, 5-phthalimidopentyl, 6-phthalimidohexyl and the like.

Alkyl at B is as defined for R, R' and $R^1$.

Alkoxy at B is as defined for R, R' and $R^1$.

Aralkyl at B is as defined for R, R' and $R^1$.

Aralkyloxy at B is as defined for $R^3$ and $R^4$.

Aminoalkyl at B is as defined for L.

Hydroxyalkyl at B is as defined for $R^{10}$ and $R^{11}$.

Alkanoyloxyalkyl at B is that wherein linear or branched alkyl having 1 to 6 carbon atoms is substituted by alkanoyloxy having alkanoyl moiety having 2 to 6 carbon atoms, which is exemplified by acetyloxymethyl, propionyloxymethyl, butyryloxymethyl, valeryloxymethyl, pivaloyloxymethyl, acetyloxyethyl, propionyloxyethyl, butyryloxyethyl, valeryloxyethyl, pivaloyloxyethyl and the like.

Alkoxycarbonylalkyl at B is that wherein linear or branched alkyl having 1 to 6 carbon atoms is substituted by alkoxycarbonyl having alkoxy moiety having 1 to 6 carbon atoms, which is exemplified by methoxycarbonylmethyl, ethoxycarbonylmethyl, propoxycarbonylmethyl, isopropoxycarbonylmethyl, butoxycarbonylmethyl, isobutoxycarbonylmethyl, sec-butoxycarbonylmethyl, tert-butoxycarbonylmethyl, pentyloxycarbonylmethyl, hexyloxycarbonylmethyl, methoxycarbonylethyl, ethoxycarbonylethyl, propoxycarbonylethyl, isopropoxycarbonylethyl, butoxycarbonylethyl, isobutoxycarbonylethyl, sec-butoxycarbonylethyl, tert-butoxycarbonylethyl, pentyloxycarbonylethyl, hexyloxycarbonylethyl and the like.

Halogen at $Q^1$, $Q^2$ and $Q^3$ is as defined for R, R' and $R^1$.

Aralkyloxy at $Q^1$ and $Q^2$ is as defined for $R^3$ and $R^4$.

Alkoxy at $Q^3$ is as defined for R, R' and $R^1$.

Alkylene at W, X and Y is linear or branched alkylene having 1 to 6 carbon atoms, which is exemplified by methylene, ethylene, trimethylene, propylene, tetramethylene, pentamethylene, hexamethylene and the like.

Alkenylene at Y is linear or branched alkenylene having 2 to 6 carbon atoms, which is exemplified by vinylene, propenylene, butenylene, pentenylene and the like.

Alkyl at Rb is as defined for R, R' and $R^1$.

Aralkyl at Rb is as defined for R, R' and $R^1$.

Aminoalkyl at Rb is as defined for L.

Mono- or dialkylaminoalkyl at Rb is as defined for L.

The heterocycle when single ring containing nitrogen at Rc is pyridine, pyrimidine, pyridazine, triazine, pyrazole, triazole and the like, and when it is a condensed ring, it is exemplified by pyrrolopyridine (e.g., 1H-pyrrolo[2,3-b]pyridine, 1H-pyrrolo[3,2-b]pyridine, 1H-pyrrolo[3,4-b]pyridine and the like), pyrazolopyridine (e.g., 1H-pyrazolo[3,4-b]pyridine, 1H-pyrazolo[4,3-b]pyridine and the like), imidazopyridine (e.g., 1H-imidazo[4,5-b]pyridine and the like), pyrrolopyrimidine (e.g., 1H-pyrrolo[2,3-d]pyrimidine, 1H-pyrrolo[3,2-d]pyrimidine, 1H-pyrrolo[3,4-d]pyrimidine and the like), pyrazolopyrimidine (e.g., 1H-pyrazolo[3,4-d]pyrimidine, pyrazolo[1,5-a]pyrimidine, 1H-pyrazolo[4,3-d]pyrimidine and the like), imidazopyrimidine (e.g., imidazo[1,2-a]pyrimidine, 1H-imidazo[4,5-d]pyrimidine and the like), pyrrolotriazine (e.g., pyrrolo[1,2-a]-1,3,5-triazine, pyrrolo[2,1-f]-1,2,4-triazine), pyrazolotriazine (e.g., pyrazolo[1,5-a]-1,3,5-triazine and the like), triazolopyridine (e.g., 1H-1,2,3-triazolo[4,5-b]pyridine and the like), triazolopyrimidine (e.g., 1,2,4-triazolo[1,5-a]pyrimidine, 1,2,4-triazolo[4,3-a]pyrimidine, 1H-1,2,3-triazolo[4,5-d]pyrimidine and the like), cinnoline, quinazoline, quinoline, pyridopyridazine (e.g., pyrido[2,3-c]pyridazine and the like), pyridopyrazine (e.g., pyrido[2,3-b]pyrazine and the like), pyridopyrimidine (e.g., pyrido[2,3-d]pyrimidine, pyrido[3,2-d]pyrimidine and the like), pyrimidopyrimidine (e.g., pyrimido[4,5-d]pyrimidine, pyrimido[5,4-d]pyrimidine and the like), pyrazinopyrimidine (e.g., pyrazino[2,3-d]pyrimidine and the like), naphthyridine (e.g., 1,8-naphthyridine and the like), tetrazolopyrimidine (e.g., tetrazolo[1,5-a]pyrimidine and the like), thienopyridine (e.g., thieno[2,3-b]pyridine and the like), thienopyrimidine (e.g., thieno[2,3-d]pyrimidine and the like), thiazolopyridine (e.g., thiazolo[4,5-b]pyridine, thiazolo[5,4-b]pyridine and the like), thiazolopyrimidine (e.g., thiazolo[4,5-d]pyrimidine, thiazolo[5,4-d]pyrimidine and the like), oxazolopyridine (e.g., oxazolo[4,5-b]pyridine, oxazolo[5,4-b]pyridine and the like), oxazolopyrimidine (e.g., oxazolo[4,5-d]pyrimidine, oxazolo[5,4-d]pyrimidine and the like), furopyridine (e.g., furo[2,3-b]pyridine, furo[3,2-b]pyridine and the like), furopyrimidine (e.g., furo[2,3-d]pyrimidine, furo[3,2-d]pyrimidine and the like), 2,3-dihydropyrrolopyridine (e.g., 2,3-dihydro-1H-pyrrolo[2,3-b]pyridine, 2,3-dihydro-1H-pyrrolo[3,2-b]pyridine and the like), 2,3-dihydropyrrolopyrimidine (e.g., 2,3-dihydro-1H-pyrrolo[2,3-d]pyrimidine, 2,3-dihydro-1H-pyrrolo[3,2-d]pyrimidine and the like), 5,6,7,8-tetrahydropyrido[2,3-d]pyrimidine, 5,6,7,8-tetrahydro-1,8-naphthyridine, 5,6,7,8-tetrahydroquinoline and the like. When these rings form a hydrogenated aromatic ring, the carbon atom in the ring may be carbonyl and includes, for example, 2,3-dihydro-2-oxopyrrolopyridine, 2,3-dihydro-2,3-dioxopyrrolopyridine, 7,8-dihydro-7-oxo-1,8-naphthyridine, 5,6,7,8-tetrahydro-7-oxo-1,8-naphthyridine and the like, with preference given to pyridin and pyrrolopyridine.

These rings may be substituted by a substituent such as halogen, alkyl, alkoxy, aralkyl, haloalkyl, nitro, amino, alkylamino, cyano, formyl, acyl, aminoalkyl, mono- or dialkylaminoalkyl, azide, carboxy, alkoxycarbonyl, carbamoyl, alkylcarbamoyl, alkoxyalkyl (e.g., methoxymethyl, methoxyethyl, methoxypropyl, ethoxymethyl, ethoxyethyl, ethoxypropyl and the like), optionally substituted hydrazino and the like.

As used herein, the substituent of the optionally substituted hydrazino includes alkyl, aralkyl, nitro, cyano and the like, wherein alkyl and aralkyl are as defined for R, R' and $R^1$ and exemplified by methylhydrazino, ethylhydrazino, benzylhydrazino and the like.

The compound of the formula (I) [inclusive of the compounds of the formula (I')] is exemplified by the following compounds.

(1) 4-(2-pyridylcarbamoyl)piperidine
(2) 1-benzyloxycarbonyl-4-(4-pyridylcarbamoyl)piperidine
(3) 1-benzoyl-4-(4-pyridylcarbamoyl)piperidine
(4) 1-propyl-4-(4-pyridylcarbamoyl)piperidine
(5) [3-(2-(2-thienylmethyl)phenoxy)-2-hydroxypropyl]-4-(4-pyridylcarbamoyl)piperidine
(6) 4-(4-pyridylcarbamoyl)piperidine
(7) 1-benzyl-4-(4-pyridylcarbamoyl)-1,2,5,6-tetrahydropyridine
(8) 3-(4-pyridylcarbamoyl)piperidine
(9) 1-benzyl-3-(4-pyridylcarbamoyl)piperidine
(10) 1-(2-(4-benzyloxyphenoxy)ethyl)-4-(N-(2-pyridyl)-N-benzylcarbamoyl)pyridine
(11) 1-formyl-4-(4-pyridylcarbamoyl)piperidine
(12) 4-(3-pyridylcarbamoyl)piperidine
(13) 1-isopropyl-4-(4-pyridylcarbamoyl)piperidine
(14) 1-methyl-4-(4-pyridylcarbamoyl)piperidine
(15) 1-hexyl-4-(4-pyridylcarbamoyl)piperidine
(16) 1-benzyl-4-(4-pyridylcarbamoyl)piperidine
(17) 1-(2-phenylethyl)-4-(4-pyridylcarbamoyl)piperidine
(18) 1-(2-(4-methoxyphenyl)ethyl)-4-(4-pyridylcarbamoyl)piperidine
(19) 1-(2-(4-methoxyphenyl)ethyl)-4-(2-pyridylcarbamoyl)piperidine
(20) 1-(2-(4-chlorophenyl)ethyl)-4-(4-pyridylcarbamoyl)piperidine
(21) 1-diphenylmethyl-4-(2-pyridylcarbamoyl)piperidine
(22) 1-[2-(4-(5-methyl-3-oxo-2,3,4,5-tetrahydropyridazin-6-yl)phenyl)ethyl]-4-(2-pyridylcarbamoyl)piperidine
(23) 1-(4-(4,5-dihydro-2-furyl)phenyl)-4-(4-pyridylcarbamoyl)piperidine
(24) 1-(2-nitrophenyl)-4-(4-pyridylcarbamoyl)piperidine
(25) 1-(2-aminophenyl)-4-(4-pyridylcarbamoyl)piperidine
(26) 1-nicotinoyl-4-(4-pyridylcarbamoyl)piperidine
(27) 1-isonicotinoyl-4-(4-pyridylcarbamoyl)piperidine
(28) 1-(3,4,5-trimethoxybenzoyl)-4-(4-pyridylcarbamoyl)piperidine
(29) 1-acetyl-4-(4-pyridylcarbamoyl)piperidine
(30) 1-(3-(4-fluorobenzoyl)propyl)-4-(4-pyridylcarbamoyl)piperidine
(31) 1-(3-(4-fluorobenzoyl)propyl)-4-(2-pyridylcarbamoyl)piperidine
(32) 1-(1-(4-hydroxybenzoyl)ethyl)-4-(2-pyridylcarbamoyl)piperidine
(33) 1-(1-(4-benzyloxybenzoyl)ethyl)-4-(2-pyridylcarbamoyl)piperidine
(34) 1-(2-(4-hydroxyphenoxy)ethyl)-4-(2-pyridylcarbamoyl)piperidine
(35) 1-(4-(4-fluorophenyl)-4-hydroxybutyl)-4-(4-pyridylcarbamoyl)piperidine
(36) 1-(1-methyl-2-(4-hydroxyphenyl)-2-hydroxyethyl)-4-(2-pyridylcarbamoyl)piperidine
(37) 1-cinnamyl-4-(2-pyridylcarbamoyl)piperidine
(38) 1-(2-hydroxy-3-phenoxypropyl)-4-(4-pyridylcarbamoyl)piperidine
(39) 1-(2-hydroxy-3-phenoxypropyl)-4-(3-pyridylcarbamoyl)piperidine
(40) 1-(2-hydroxy-3-phenoxypropyl)-4-(2-pyridylcarbamoyl)piperidine
(41) 1-(2-phenylethyl)-4-[N-(2-pyridyl)-N-(2-(N,N-dimethylamino)ethyl)carbamoyl]piperidine
(42) 1-benzyloxycarbonyl-4-(2-pyridylcarbamoyl)piperidine
(43) 1-(3-chlorophenyl)carbamoyl-4-(4-pyridylcarbamoyl)piperidine
(44) 1-[N-(2-pyridyl)-N-(2-(N,N-dimethylamino)ethyl)carbamoyl]piperidine
(45) 1-methyl-4-(4-pyridylcarbamoyl)-1,2,5,6-tetrahydropyridine
(46) 1-nicotinoyl-3-(4-pyridylcarbamoyl)piperidine
(47) 1-[2-(4-fluorobenzoyl)ethyl]-4-(4-pyridylcarbamoyl)piperidine
(48) 1-(6-chloro-2-methylimidazo[1,2-a]pyridine-3-carbonyl)-4-(4-pyridylcarbamoyl)piperidine
(49) 1-(4-nitrobenzyl)-4-(4-pyridylcarbamoyl)piperidine
(50) 1-hexyl-4-(4-pyridylcarbamoyl)piperidine
(51) 1-benzyloxycarbonyl-4-(2-chloro-4-pyridylcarbamoyl)piperidine
(52) 4-(2-chloro-4-pyridylcarbamoyl)piperidine
(53) 1-(2-chloronicotinoyl)-4-(4-pyridylcarbamoyl)piperidine
(54) 3-(2-chloro-4-pyridylcarbamoyl)piperidine
(55) 1-(4-phthalimidobutyl)-4-(4-pyridylcarbamoyl)piperidine
(56) 1-(3,5-di-tert-butyl-4-hydroxycinnamoyl)-4-(4-pyridylcarbamoyl)piperidine
(57) 1-carbamoylmethyl-4-(4-pyridylcarbamoyl)piperidine
(58) 1-benzyloxycarbonyl-4-(5-nitro-2-pyridylcarbamoyl)piperidine
(59) 4-(5-nitro-2-pyridylcarbamoyl)piperidine
(60) trans-4-benzyloxycarboxamidomethyl-1-(4-pyridylcarbamoyl)cyclohexane
(61) trans-4-aminomethyl-1-(4-pyridylcarbamoyl)cyclohexane
(62) trans-4-formamidomethyl-1-(4-pyridylcarbamoyl)cyclohexane
(63) trans-4-dimethylaminomethyl-1-(4-pyridylcarbamoyl)cyclohexane
(64) N-benzylidene-trans-(4-pyridylcarbamoyl)cyclohexylmethylamine
(65) trans-4-benzylaminomethyl-1-(4-pyridylcarbamoyl)cyclohexane
(66) trans-4-isopropylaminomethyl-1-(4-pyridylcarbamoyl)cyclohexane

(67) trans-4-nicotinoylaminomethyl-1-(4-pyridylcarbamoyl)cyclohexane
(68) trans-4-cyclohexylaminomethyl-1-(4-pyridylcarbamoyl)cyclohexane
(69) trans-4-benzyloxycarboxamide-1-(4-pyridylcarbamoyl)cyclohexane
(70) trans-4-amino-1-(4-pyridylcarbamoyl)cyclohexane
(71) trans-4-(1-aminoethyl)-1-(4-pyridylcarbamoyl)cyclohexane
(72) trans-4-aminomethyl-cis-2-methyl-1-(4-pyridylcarbamoyl)cyclohexane
(73) (+)-trans-4-(1-benzyloxycarboxamidopropyl)-1-cyclohexanecarboxylic acid
(74) (+)-trans-4-(1-benzyloxycarboxamidopropyl)-1-(4-pyridylcarbamoyl)cyclohexane
(75) (−)-trans-4-(1-benzyloxycarboxamidpropyl)-1-(4-pyridylcarbamoyl)cyclohexane
(76) (+)-trans-4-(1-aminopropyl)-1-(4-pyridylcarbamoyl)cyclohexane
(77) (−)-trans-4-(1-aminopropyl)-1-(4-pyridylcarbamoyl)cyclohexane
(78) (−)-trans-4-(1-benzyloxycarboxamidoethyl)-1-(4-pyridylcarbamoyl)cyclohexane
(79) (+)-trans-4-(1-benzyloxycarboxamidoethyl)-1-(4-pyridylcarbamoyl)cyclohexane
(80) (+)-trans-4-(1-aminoethyl)-1-(4-pyridylcarbamoyl)cyclohexane
(81) (−)-trans-4-(1-aminoethyl)-1-(4-pyridylcarbamoyl)cyclohexane
(82) trans-4-(4-chlorobenzoyl)aminomethyl-1-(4-pyridylcarbamoyl)cyclohexane
(83) trans-4-aminomethyl-1-(2-pyridylcarbamoyl)cyclohexane
(84) trans-4-benzyloxycarboxamidomethyl-1-(2-pyridylcarbamoyl)cyclohexane
(85) trans-4-methylaminomethyl-1-(4-pyridylcarbamoyl)cyclohexane
(86) trans-4-(N-benzyl-N-methylamino)methyl-1-(4-pyridylcarbamoyl)cyclohexane
(87) trans-4-aminomethyl-1-(3-pyridylcarbamoyl)cyclohexane
(88) trans-4-aminomethyl-1-[(3-hydroxy-2-pyridyl)carbamoyl]-cyclohexane
(89) trans-4-benzyloxycarboxamidomethyl-1-(3-pyridylcarbamoyl)cyclohexane
(90) trans-4-benzyloxycarboxamidomethyl-1-[(3-benzyloxy-2-pyridyl)carbamoyl]cyclohexane
(91) trans-4-phthalimidomethyl-1-(4-pyridylcarbamoyl)cyclohexane
(92) trans-4-benzyloxycarboxamidomethyl-1-(3-methyl-4-pyridylcarbamoyl)cyclohexane
(93) trans-4-aminomethyl-1-(3-methyl-4-pyridylcarbamoyl)cyclohexane
(94) 4-(trans-4-benzyloxycarboxamidomethylcyclohexylcarbonyl)amino-2,6-dimethylpyridine-N-oxide
(95) 4-(trans-4-aminomethylcyclohexylcarbonyl)amino-2,6-dimethylpyridine-N-oxide
(96) trans-4-aminomethyl-1-(2-methyl-4-pyridylcarbamoyl)cyclohexane
(97) trans-4-(1-benzyloxycarboxamidoethyl)-1-(4-pyridylcarbamoyl)cyclohexane
(98) trans-4-(1-amino-1-methylethyl)-1-(4-pyridylcarbamoyl)cyclohexane
(99) trans-4-(2-aminoethyl)-1-(4-pyridylcarbamoyl)cyclohexane
(100) trans-4-(2-amino-1-methylethyl)-1-(4-pyridylcarbamoyl)cyclohexane
(101) trans-4-(1-aminopropyl)-1-(4-pyridylcarbamoyl)cyclohexane
(102) trans-4-aminomethyl-trans-1-methyl-1-(4-pyridylcarbamoyl)cyclohexane
(103) trans-4-benzylaminomethyl-cis-2-methyl-1-(4-pyridylcarbamoyl)cyclohexane
(104) trans-4-(1-benzyloxycarboxamide-1-methylethyl)-1-(4-pyridylcarbamoyl)cyclohexane
(105) trans-4-benzyloxycarboxamidomethyl-1-(N-methyl-4-pyridylcarbamoyl)cyclohexane
(106) trans-4-(1-acetamide-1-methylethyl)-1-(4-pyridylcarbamoyl)cyclohexane
(107) trans-N-(6-amino-4-pyrimidyl)-4-aminomethyl-cyclohexanecarboxamide
(108) trans-N-(1H-pyrrolo[2,3-b]pyridin-4-yl)-4-aminomethylcyclohexanecarboxamide
(109) (+)-trans-N-(1H-pyrrolo[2,3-b]pyridin-4-yl)-4-(1-aminoethyl)cyclohexanecarboxamide
(110) trans-N-(1H-pyrrolo[2,3-b]pyridin-4-yl)-4-(1-amino-1-methylethyl)cyclohexanecarboxamide
(111) trans-N-(1H-pyrazolo[3,4-b]pyridin-4-yl)-4-aminomethylcyclohexanecarboxamide
(112) (+)-trans-N-(1H-pyrazolo[3,4-b]pyridin-4-yl)-4-(1-aminoethyl)cyclohexanecarboxamide
(113) trans-N-(1H-pyrazolo[3,4-b]pyridin-4-yl)-4-(1-amino-1-methylethyl)cyclohexanecarboxamide
(114) (+)-trans-N-(2-amino-4-pyridyl)-4-(1-aminoethyl)cyclohexanecarboxamide
(115) trans-N-(1H-pyrazolo[3,4-d]pyrimidin-4-yl)-4-aminomethylcyclohexanecarboxamide
(116) (+)-trans-N-(1H-pyrazolo[3,4-d]pyrimidin-4-yl)-4-(1-aminoethyl)cyclohexanecarboxamide
(117) trans-N-(1H-pyrazolo[3,4-d]pyrimidin-4-yl)-4-(1-amino-1-methylethyl)cyclohexanecarboxamide
(118) trans-N-(4-pyrimidinyl)-4-aminomethyl- cyclohexanecarboxamide
(119) trans-N-(3-amino-4-pyridyl)-4-aminomethyl- cyclohexanecarboxamide
(120) trans-N-(7H-imidazo[4,5-d]pyrimidin-6-yl)-4-aminomethylcyclohexanecarboxamide
(121) trans-N-(3H-1,2,3-triazolo[4,5-d]pyrimidin-7-yl)-4-aminomethylcyclohexanecarboxamide
(122) trans-N-(1-benzyl-1H-pyrazolo[3,4-b]pyridin-4-yl)-4-aminomethylcyclohexanecarboxamide
(123) trans-N-(1H-5-pyrazolyl)-4-aminomethyl- cyclohexanecarboxamide
(124) trans-N-(1H-pyrazolo[3,4-b]pyridin-4-yl)-4-aminomethylcyclohexanecarboxamide
(125) trans-N-(4-pyridazinyl)-4-aminomethyl- cyclohexanecarboxamide
(126) trans-N-(7H-pyrrolo[2,3-d]pyrimidin-4-yl)-4-aminomethylcyclohexanecarboxamide
(127) trans-N-(2-amino-4-pyridyl)-4-aminomethyl- cyclohexanecarboxamide
(128) trans-N-(thieno[2,3-d]pyrimidin-4-yl)-4-aminomethylcyclohexanecarboxamide
(129) trans-N-(5-methyl-1,2,4-triazolo[1,5-a]pyrimidin-7-yl)-4-aminomethylcyclohexanecarboxamide
(130) trans-N-(3-cyano-5-methylpyrazolo[1,5-a]pyrimidin-7-yl)-4-aminomethylcyclohexanecarboxamide
(131) trans-N-(1H-pyrazolo[3,4-b]pyridin-4-yl)-4-(1-amino-1-methylethyl)cyclohexanecarboxamide
(132) trans-N-(2-(1-pyrrolidinyl)-4-pyridyl)-4-aminomethylcyclohexanecarboxamide
(133) trans-N-(2,6-diamino-4-pyrimidyl)-4-aminomethylcyclohexanecarboxamide
(134) (+)-trans-N-(7-methyl-1,8-naphthyridin-4-yl)-4-(1-aminoethyl)cyclohexanecarboxamide (135) trans-N-(1-benzyloxymethylpyrrolo[2,3-b]pyridin-4-yl)-4-aminomethylcyclohexanecarboxamide
(136) (+)-trans-N-(1-methylpyrrolo[2,3-b]pyridin-4-yl)-4-(1-aminoethyl)cyclohexanecarboxamide
(137) trans-N-benzyl-N-(2-benzylamino-4-pyridyl)-4-(1-amino-1-methylethyl)cyclohexanecarboxamide
(138) trans-N-(2-azide-4-pyridyl)-4-aminomethyl- cyclohexanecarboxamide
(139) trans-N-(2,3-dihydro-1H-pyrrolo[2,3-b]pyridin-4-yl)-4-aminomethylcyclohexanecarboxamide
(140) trans-N-(2,3-dihydro-1H-pyrrolo[2,3-b]pyridin-4-yl)-4-(1-amino-1-methylethyl)cyclohexanecarboxamide
(141-1) trans-N-(2-carboxy-4-pyridyl)-4-aminomethylcyclohexanecarboxamide
(141-2) (R)-(+)-trans-N-(3-bromo-1H-pyrrolo[2,3-b]pyridin-4-yl)-4-(1-aminoethyl)cyclohexanecarboxamide
(142) trans-N-(1H-pyrrolo[2,3-b]pyridin-4-yl)-4-guanidinomethylcyclohexanecarboxamide
(143) trans-N-(1H-pyrazolo[3,4-b]pyridin-4-yl)-4-guanidinomethylcyclohexanecarboxamide
(144) trans-N-(4-pyridyl)-4-guanidinomethyl- cyclohexanecarboxamide
(145) trans-N-(1-methylpyrrolo[2,3-b]pyridin-4-yl)-4-(guanidinomethyl)cyclohexanecarboxamide
(146) trans-N-(1H-pyrrolo[2,3-b]pyridin-4-yl)-4-(2-imidazolin-2-yl)aminomethylcyclohexanecarboxamide
(147) trans-N-(1-benzyloxymethylpyrrolo[2,3-b]pyridin-4-yl)-4-guanidinomethylcyclohexanecarboxamide
(148) trans-N-(2-amino-4-pyridyl)-4-guanidino- methylcyclohexanecarboxamide
(149) trans-N-(1-benzyloxymethyl-1H-pyrrolo[2,3-b]pyridin-4-yl)-4-(2-imidazolin-2-yl)aminomethylcyclohexanecarboxamide
(150) trans-N-(1H-pyrrolo[2,3-b]pyridin-4-yl)-4-(3-benzylguanidinomethyl)-cyclohexanecarboxamide
(151) trans-N-(1H-pyrrolo[2,3-b]pyridin-4-yl)-4-(3-phenylguanidinomethyl)-cyclohexanecarboxamide
(152) trans-N-(1H-pyrrolo[2,3-b]pyridin-4-yl)-4-(3-propylguanidinomethyl)-cyclohexanecarboxamide
(153) trans-N-(1H-pyrrolo[2,3-b]pyridin-4-yl)-4-(3-octylguanidinomethyl)-cyclohexanecarboxamide
(154) trans-N-(1-benzyloxymethylpyrrolo[2,3-b]pyridin-4-yl)-4-(2-benzyl-3-ethylguanidinomethyl)cyclohexanecarboxamide
(155) trans-N-(1H-pyrrolo[2,3-b]pyridin-4-yl)-4-(imidazol-2-yl)aminomethylcyclohexanecarboxamide
(156) trans-N-(1H-pyrrolo[2,3-b]pyridin-4-yl)-4-(thiazol-2-yl)aminomethylcyclohexanecarboxamide
(157) (R)-(+)-N-(4-pyridyl)-4-(1-aminoethyl)benzamide
(158) N-(4-pyridyl)-4-(1-amino-1-methylethyl)benzamide
(159) N-(4-pyridyl)-4-aminomethyl-2-benzyloxybenzamide
(160) N-(4-pyridyl)-4-aminomethyl-2-ethoxybenzamide
(161) (R)-(−)-N-(4-pyridyl)-4-(1-aminoethyl)-3-nitrobenzamide
(162) (R)-(−)-N-(4-pyridyl)-3-amino-4-(1-aminoethyl)benzamide
(163) (R)-(+)-N-(4-pyridyl)-4-(1-aminoethyl)-3-chlorobenzamide
(164) N-(4-pyridyl)-3-aminomethylbenzamide
(165) (R)-(+)-N-(1H-pyrrolo[2,3-b]pyridin-4-yl)-4-(1-aminoethyl)benzamide
(166) (R)-(+)-N-(1H-pyrazolo[3,4-b]pyridin-4-yl)-4-(1-aminoethyl)benzamide
(167) N-(1H-pyrazolo[3,4-b]pyridin-4-yl)-4-guanidinomethylbenzamide
(168) N-(4-pyridyl)-4-guanidinomethylbenzamide
(169) (R)-(+)-N-(4-pyridyl)-4-(1-aminoethyl)-3-fluorobenzamide
(170) N-(4-pyridyl)-4-aminomethylbenzamide
(171) N-(4-pyridyl)-4-aminomethyl-2-hydroxybenzamide
(172) N-(4-pyridyl)-4-(2-aminoethyl)benzamide
(173) N-(4-pyridyl)-4-aminomethyl-3-nitrobenzamide
(174) N-(4-pyridyl)-3-amino-4-aminomethylbenzamide
(175) (S)-(−)-N-(4-pyridyl)-4-(1-aminoethyl)benzamide
(176) (S)-(−)-N-(4-pyridyl)-2-(1-aminoethyl)benzamide
(177) (R)-(+)-N-(4-pyridyl)-4-(1-aminoethyl)-2-chlorobenzamide
(178) (R)-(+)-N-(1H-pyrrolo[2,3-b]pyridin-4-yl)-4-(1-(3-propylguanidino)ethyl)benzamide
(179) (R)-(−)-N-(1H-pyrrolo[2,3-b]pyridin-4-yl)-4-(1-aminoethyl)-3-azidebenzamide
(180) (R)-(+)-N-(4-pyridyl)-4-(1-aminoethyl)-2-nitrobenzamide
(181) (R)-(−)-N-(4-pyridyl)-4-(1-aminoethyl)-3-ethoxybenzamide
(182) (R)-(+)-N-(3-iodo-1H-pyrrolo[2,3-b]pyridin-4-yl)-4-(1-aminoethyl)benzamide
(183) (R)-(+)-N-(3-iodo-1H-pyrrolo[2,3-b]pyridin-4-yl)-4-(1-aminoethyl)-3-azidebenzamide
(184) (R)-(−)-N-(4-pyridyl)-4-(1-aminoethyl)-3-hydroxybenzamide
(185) N-(1H-pyrazolo[3,4-b]pyridin-4-yl)-4-guanidinomethyl-3-nitrobenzamide
(186) (R)-N-(1H-pyrazolo[3,4-b]pyridin-4-yl)-4-(1-guanidinoethyl)-3-nitrobenzamide
(187) (R)-N-(1H-pyrazolo[3,4-b]pyridin-4-yl)-4-(1-aminoethyl)-2-nitrobenzamide
(188) N-(1H-pyrazolo[3,4-b]pyridin-4-yl)-4-guanidinobenzamide
(189) (R)-N-(1H-pyrazolo[3,4-b]pyridin-4-yl)-4-(1-aminoethyl)-3-nitrobenzamide
(190) (R)-N-(1H-pyrazolo[3,4-b]pyridin-4-yl)-4-(1-guanidinoethyl)benzamide
(191) N-(1H-pyrazolo[3,4-b]pyridin-4-yl)-4-(1-amino-2-hydroxyethyl)benzamide
(192) N-(1H-pyrazolo[3,4-b]pyridin-4-yl)-4-aminomethyl-3-nitrobenzamide
(193) N-(1H-pyrrolo[2,3-b]pyridin-4-yl)-4-piperidinecarboxamide
(194) N-(1H-pyrazolo[3,4-b]pyridin-4-yl)-4-piperidinecarboxamide
(195) N-(1H-pyrazolo[3,4-b]pyridin-4-yl)-1-aminoacetyl-4--piperidinecarboxamide
(196) N-(1-methoxymethyl-1H-pyrazolo[3,4-b]pyridin-4-yl)-4-piperidinecarboxamide
(197) N-(2,3-dihydro-1H-pyrrolo[2,3-b]pyridin-4-yl)-4-piperidinecarboxamide
(198) N-(1H-pyrrolo[2,3-b]pyridin-4-yl)-1-(2-phenylethyl)-4-piperidinecarboxamide
(199) N-(1H-pyrrolo[2,3-b]pyridin-4-yl)-1-amidino-4-piperidinecarboxamide
(200) N-(1H-pyrrolo[2,3-b]pyridin-4-yl)-1-(3-phenylpropyl)-4-piperidinecarboxamide
(201) N-(1H-pyrrolo[2,3-b]pyridin-4-yl)-1-benzyl-4-piperidinecarboxamide
(202) N-(1H-pyrazolo[3,4-b]pyridin-4-yl)-1-(2-phenylethyl)-4-piperidinecarboxamide
(203) N-(1H-pyrazolo[3,4-b]pyridin-4-yl)-1-(3-phenylpropyl)-4-piperidinecarboxamide Preferred are compounds (80), (109), (110), (112), (115), (142), (143), (144), (145), (153), (157), (163), (165), (166) and (179).

The compound having a Rho kinase inhibitory activity may be a pharmaceutically acceptable acid addition salt, wherein the acid is exemplified by inorganic acid such as hydrochloric acid, hydrobromic acid, sulfuric acid and the like, and organic acid such as methanesulfonic acid, fumaric acid, maleic acid, mandelic acid, citric acid, tartaric acid, salicylic acid and the like. A compound having a carboxylic group can be converted to a salt with a metal such as sodium, potassium, calcium, magnesium, aluminum and the like, a salt with an amino acid such as lysine and the like. Further, monohydrate, dihydrate, 1/2 hydrate, 1/3 hydrate, 1/4 hydrate, 2/3 hydrate, 3/2 hydrate, 6/5 hydrate and the like are encompassed in the present invention.

The compound of the formula (I) can be synthesized by a method described in, for example, JP-A-62-89679, JP-A-3-218356, JP-A-5-194401, JP-A-6-41080, WO95/28387, WO98/06433 and the like.

When the above-mentioned compound having a Rho kinase inhibitory activity has an optical isomer, its racemate or cis-trans isomers, all of them can be used in the present invention. These isomers can be isolated by a conventional method or can be produced using starting materials of the isomers.

A compound having a Rho kinase inhibitory activity, particularly, a compound of the formula (I), an isomer thereof and/or a pharmaceutically acceptable acid addition salt thereof have intraocular pressure lowering action, optic disc blood flow improving action and aqueous outflow promoting action in mammals inclusive of human, cow, horse, dog, mouse, rat and the like. Therefore, they can be used as an agent for the prophylaxis and treatment of various types of glaucoma, such as primary open angle glaucoma, normal pressure glaucoma, hypersecretion glaucoma, ocular hypertension, acute angle closure glaucoma, chronic angle closer glaucoma, plateau iris syndrome, combined-mechanism glaucoma, steroid glaucoma, capsular glaucoma, pigmentary glaucoma, secondary glaucoma associated with amyloidosis, neovascular glaucoma, malignant glaucoma and the like.

The agent for the prophylaxis and treatment of glaucoma of the present invention is administered orally or parenterally. The dosage form may be, for example, oral preparation such as tablet, capsule, syrup and the like, or parenteral preparation such as liquid injection (e.g., solution, emulsion, suspension and the like), external agent [e.g., ointment (particularly eye ointment), eye drop and the like], and the like. In consideration of the influence and effect on other circulatory systems, the dosage form of administration to local site in the eye is preferable. The dosage form of eye drop or eye ointment is particularly preferable.

A preparation having the aforementioned dosage form can be prepared by mixing the inventive compound with an additive necessary for formulating a preparation, such as typical carrier, excipient, binder, stabilizer and the like and by following a conventional method. For example, the compound having a Rho kinase inhibitory activity is mixed with a pharmaceutically acceptable carrier (e.g., excipient, binder, disintegrator, corrective, corrigent, emulsifier, diluent, solubilizer and the like) to give a pharmaceutical composition or a pharmaceutical preparation in the form of tablet, pill, powder, granule, capsule, troche, syrup, liquid, emulsion, suspension, injection (e.g., liquid, suspension and the like), suppository, inhalant, percutaneous absorber, eye drop, eye ointment and the like in the form suitable for oral or parenteral preparation.

When preparing a solid preparation, additives such as sucrose, lactose, cellulose sugar, D-mannitol, maltitol, dextran, starches, agar, arginates, chitins, chitosans, pectines, tragacanth gum, gum arabic, gelatins, collagens, casein, albumin, calcium phosphate, sorbitol, glycine, carboxymethylcellulose, polyvinylpyrrolidone, hydroxypropylcellulose, hydroxypropylmethylcellulose, glycerol, polyethyleneglycol, sodium hydrogencarbonate, magnesium stearate, talc and the like are used. Tablets can be applied with a typical coating, where necessary, to give sugar coated tablets, enteric tablets, film-coated tablets, two-layer tablets and multi-layer tablets.

When preparing a semi-solid preparation, animal and plant fats and oils (e.g., olive oil, corn oil, castor oil and the like), mineral fats and oils (e.g., petrolatum, white petrolatum, solid paraffin and the like), wax (e.g., jojoba oil, carnauba wax, bee wax and the like), partly or entirely synthesized glycerol fatty acid esters (e.g., lauric acid, myristic acid, palmitic acid and the like), and the like are used. Examples of commercially available products of these include Witepsol (manufactured by Dynamitnovel Ltd.), Farmazol (NOF Corporation) and the like.

When preparing a liquid preparation, an additive, such as sodium chloride, glucose, sorbitol, glycerol, olive oil, propylene glycol, ethyl alcohol and the like, is used.

The liquid preparation may be, for example, injection, eye drop and the like.

When preparing an injection, a sterile aqueous solution such as physiological saline, isotonic solution, oil (e.g., sesame oil and soybean oil) and the like are used. Where necessary, a suitable suspending agent such as sodium carboxymethylcellulose, nonionic surfactant, solubilizer (e.g., benzyl benzoate and benzyl alcohol), and the like can be concurrently used.

Moreover, when an eye drop is prepared, an aqueous liquid or solution is used, which is particularly a sterile injectable aqueous solution. The eye drop can appropriately contain various additives such as buffer, stabilizer, wetting agent, emulsifier, suspending agent, surfactant, isotonicity agent, preservative and thickener.

The buffer may be, for example, phosphate buffer, borate buffer, citrate buffer, tartrate buffer, acetate buffer, amino acid and the like.

The stabilizer may be, for example, sodium edetate, citric acid and the like.

The wetting agent may be, for example, glycerol and the like.

The emulsifier may be, for example, polyvinylpyrrolidone and the like.

The suspending agent may be, for example, hydroxypropylmethylcellulose, methylcellulose and the like.

The surfactant may be, for example, polysorbate 80, polyoxyethylene hydrogenated castor oil and the like.

The isotonicity agent may be, for example, saccharides such as sorbitol, glucose, mannitol and the like, polyhydric alcohols such as glycerol, propylene glycol and the like, salts such as sodium chloride and the like, and the like.

The preservative may be, for example, quaternary ammonium salt such as benzalkonium chloride, benzethonium chloride and the like, p-hydroxybenzoate such as methyl p-hydroxybenzoate, ethyl p-hydroxybenzoate and the like, benzyl alcohol, phenethyl alcohol, sorbic acid and salts thereof, thimerosal, chlorobutanol and the like.

The thickener may be, for example, hydroxyethylcellulose, hydroxypropylcellulose, methylcellulose, hydroxypropylmethylcellulose, carboxymethylcellulose, salts thereof and the like.

When in use as an eye drop, pH is preferably adjusted generally to about 4–9, preferably about 6–8.5.

When the preparation is an eye ointment, an ointment base (e.g., petrolatum, lanolin, plastibase and the like), a preservative (e.g., benzalkonium chloride, p-hydroxybenzoate, chlorobutanol and the like), and the like are appropriately selected and used for production.

The agent for the prophylaxis and treatment of glaucoma of the present invention contains an active ingredient in a proportion of 0.0001–100 wt %, suitably 0.001–50 wt %, of the preparation. While the dose and administration frequency vary depending on symptom, age, body weight and administration form, when it is used as an eye drop for an adult, a preparation containing a compound having a Rho kinase inhibitory activity in a proportion of 0.0001–10 w/v %, preferably 0.001–1 w/v %, is administered several times a day, preferably 1–6 times a day, by several drops, preferably 1–3 drops, each time. When it is used as an eye ointment, a preparation containing this compound in a proportion of 0.0001–10 w/w %, preferably 0.001–1 w/w %, can be applied several times a day, preferably 1–6 times a day.

EXAMPLES

The present invention is explained in detail by referring to examples and experimental examples. The present invention is not limited in any way by these examples.

Example 1

Eye Drop 1

(+)-trans-4-(1-Aminoethyl)-1-(4-pyridylcarbamoyl) cyclohexane 2HCl 1H$_2$O (hereinafter Compound A), which is a compound having a Rho kinase inhibitory activity, was dissolved in distilled water for injection. The pH was adjusted to 7 with sodium hydroxide and an eye drop having the following composition was prepared.

| | |
|---|---|
| Compound A | 0.5 g |
| Sodium dihydrogenphosphate 2 hydrate | 0.1 g |
| Sodium chloride | 0.9 g |
| distilled water for injection | appropriate amount |
| Total amount | 100 ml |

Example 2

Eye Drop 2

In the same manner as in Example 1, an eye drop containing Compound A at a concentration of 0.1% was prepared.

Example 3

Eye Drop 3

In the same manner as in Example 1, an eye drop containing Compound A at a concentration of 0.03% was prepared.

Example 4

Eye Drop 4

In the same manner as in Example 1, an eye drop containing (+)-trans-N-(1H-pyrrolo[2,3-b]pyridin-4-yl)-4-(1-aminoethyl)cyclohexanecarboxamide 2HCl 6/5H$_2$O (hereinafter Compound B), which is a compound having a Rho kinase inhibitory activity, at a concentration of 0.03% was prepared.

Example 5

Eye Drop 5

In the same manner as in Example 1, an eye drop containing (R)-(+)-N-(4-pyridyl)-4-(1-aminoethyl) benzamide 2HCl (hereinafter Compound C), which is a compound having a Rho kinase inhibitory activity, at a concentration of 0.1% was prepared.

Example 6

Eye Drop 6

In the same manner as in Example 5, an eye drop containing Compound C at a concentration of 0.03% was prepared.

Example 7

Eye Drop 7

In the same manner as in Example 1, an eye drop containing (R)-(+)-N-(1H-pyrrolo[2,3-b]pyridin-4-yl)-4-(1-aminoethyl)benzamide 2HCl 1H$_2$O (hereinafter Compound D), which is a compound having a Rho kinase inhibitory activity, at a concentration of 0.03% was prepared.

Example 8

Tablets

The Compound A, lactose, corn starch and crystalline cellulose were mixed, kneaded with polyvinylpyrrolidone K30 paste solution and passed through a 20-mesh sieve for granulation. After drying at 50° C. for 2 hours, the granules were passed through a 24-mesh sieve, and talc and magnesium stearate were added. Using a φ7 mm punch, tablets weighing 120 mg per tablet were prepared.

| | |
|---|---|
| Compound A | 10.0 mg |
| Lactose | 50.0 mg |
| Corn starch | 20.0 mg |
| Crystalline cellulose | 29.7 mg |
| Polyvinylpyrrolidone K30 | 5.0 mg |
| Talc | 5.0 mg |
| Magnesium stearate | 0.3 mg |
| | 120.0 mg |

Formulation Example 9

Capsules

The Compound A, lactose and corn starch were mixed, kneaded with polyvinylpyrrolidone K30 paste solution and passed through a 20-mesh sieve for granulation. After drying at 50° C. for 2 hours, the granules were passed through a 24-mesh sieve and talc and magnesium stearate were added. The mixture was filled in hard capsules (No. 4) to give capsules weighing 120 mg.

| | |
|---|---|
| Compound A | 10.0 mg |
| Lactose | 70.0 mg |
| Corn starch | 35.0 mg |
| Polyvinylpyrrolidone K30 | 2.0 mg |

|  |  |
|---|---|
| Talc | 2.7 mg |
| Magnesium stearate | 0.3 mg |
|  | 120.0 mg |

Experimental Example 1

Effect on Normal Intraocular Pressure of Coloured Rabbit

Experiment Method

Male Dutch coloured rabbits (body weight about 2 kg) were used. The rabbits were placed in a holding box for 3–5 hr a day for acclimation from one week prior to the test. The rabbits that showed steady intraocular pressure as measured by a tonometer [pneumatonograph (manufactured by Alcon Lab. Inc.)] were selected and used for the test. After measurement of the initial value of the intraocular pressure, the eye drop (50 μl) of Example 1 was instilled into one eye, and a base, which was the eye drop of Example 1 except Compound A, was instilled into the other eye in the same manner and taken as the control eye. The intraocular pressure was measured with time at 30, 60, 90 and 120 min after instillation and thereafter at 60 min intervals until the intraocular pressure returned to the initial value, and the duration of the effect was examined.

Experiment Result

The effect of the eye drop of Example 1 on the normal intraocular pressure is shown in FIG. 1. When compared to the control eye at 60 min after instillation, the maximum significant intraocular pressure lowering action of 5 mmHg was observed. For 180 min after instillation, a significant intraocular pressure lowering action as compared to the control eye was found. At 360 min after instillation, the intraocular pressure was almost the same as in the control eye and returned to the initial value.

Experimental Example 2

Effect on Blood Flow of Normal Optic Disc of Coloured Rabbit

Experiment Method

Male Dutch coloured rabbits (body weight about 2 kg) were used. The eye drop (50 μl) of Example 1 was instilled into one eye, and a base, which was the eye drop of Example 1 except Compound A, was instilled into the other eye in the same manner and taken as the control eye. Using a laser speckle microcirculation analyzer, the blood flow of optic disc was measured at 30, 60, 90 and 120 min after instillation and thereafter at 60 min intervals till 300 min after the instillation.

Experiment Result

Figure 2:
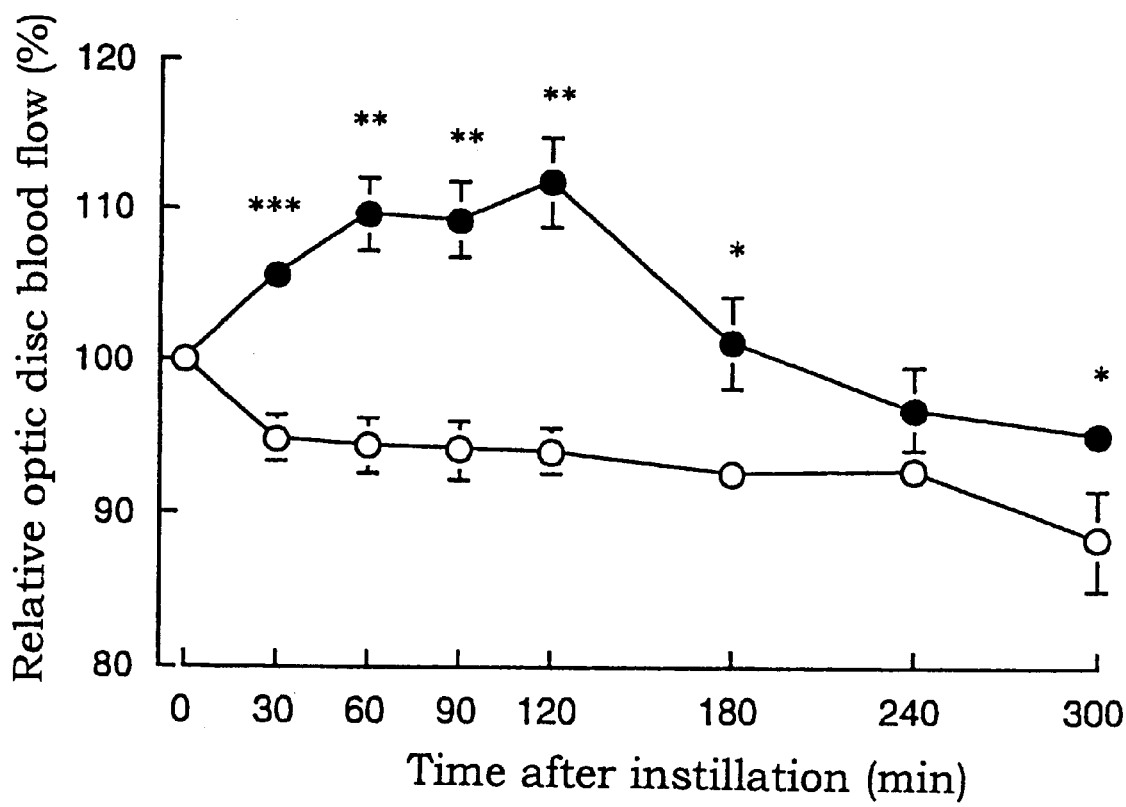
FIG. 2 is a graph showing the effect of the eye drop of Example 1 on the optic disc blood flow kinetic, wherein the ordinate shows relative optic disc blood flow, the abscissa shows time after instillation, ● shows the eye instilled with the eye drop of Example 1 and ○ shows control eye (n=6, *p<0.05, p<0.01, *p<0.001).

The effect of the eye drop of Example 1 on the optic disc blood flow kinetic is shown in FIG. 2. When compared to the control eye, a 11% blood flow increasing action was found at 30 min after instillation, and a 15% significant blood flow increasing action was found at 60 min after instillation. The blood flow increased most (18%) at 120 min after instillation. The effect gradually decreased thereafter, but a significant blood flow increasing action was observed for 180 min after the instillation as compared to the control eye.

Experimental Example 3

Effect on Carbachol Contraction of Extracted Ciliary Muscle of White Rabbit

Experiment Method

Male Japanese white rabbits (body weight about 2 kg) were euthanized by intravenous administration of an excess pentobarbital sodium. The eyeball was enucleated immediately thereafter and preserved in a Krebs solution (NaCl:112 mM, KCl:5.9 mM, $CaCl_2$ $2H_2O$:2.0 mM, $MgCl_2$ $6H_2O$:1.2 mM, $NaH_2PO_4$ $2H_2O$:1.2 mM, $NaHCO_3$:25 mM, Glucose:11.5 mM). The ciliary body separated from the eyeball was hung in a Magnus bath filled with the Krebs solution and equilibrated under a 20–30 mg resting tension. The changes in the tension of the preparation was measured with a transducer and recorded on a pen recorder via an amplifier. As the contraction drug, carbachol was used, and the inhibitory action on the dose dependent response of phasic contraction was studied. The test drug was (+)-trans-4-(1-aminoethyl)-1-(4-pyridylcarbamoyl)cyclohexane 2HCl $1H_2O$ (Compound A), which was added to the Magnus bath 5 min before addition of carbachol.

Experiment Result

Figure 3:
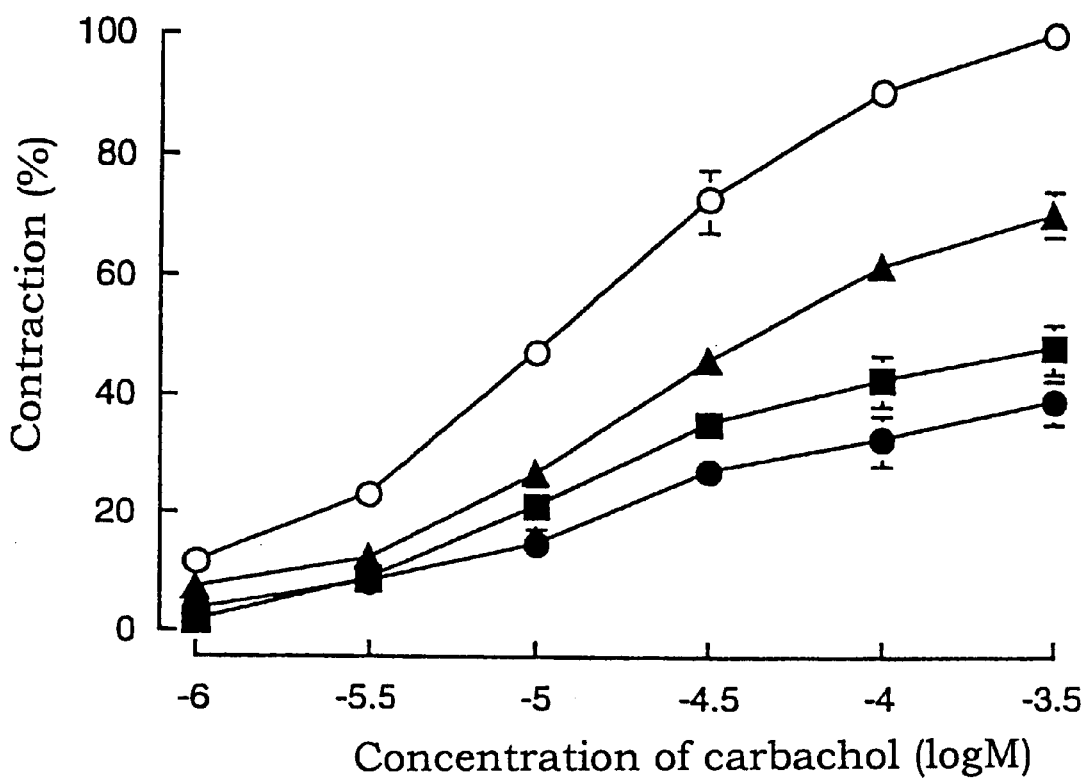
FIG. 3 is a graph showing the effect of Compound A on ciliary muscle contraction by carbachol, wherein the ordinate shows contraction rate of ciliary muscle, the abscissa shows concentration of carbachol, ○ shows control, ● shows addition of 1×10$^{-5}$ M Compound A, ■ shows addition of 3×10$^{-6}$ M Compound A and ▲ shows addition of 1×10$^{-6}$ M Compound A.

The effect of Compound A on the carbachol contraction is shown in FIG. 3. The ciliary muscle showed a dose dependent contraction by $10^{-6}$–$3\times10^{-4}$ M carbachol and Compound A showed non-competitive antagonism against carbachol contraction. The $IC_{50}$ of Compound A against carbachol contraction was $2.8\times10^{-6}$ M.

The contraction and relaxation of the ciliary muscle play an important role in aqueous outflow. By the relaxation of the ciliary muscle, the aqueous outflow via trabecular meshwork can be inhibited but that via uveosclera is promoted (Takeshi Yoshitomi, Neuro-ophthalmol. Jpn., 15(1), 76–81, 1998). The relaxation of the ciliary muscle that promotes aqueous outflow is considered to result in lowering of the intraocular pressure.

In general, 1/1000 of eye drop is said to be transferred into anterior chamber (Kouji Honda: Practical Ophthalmology, Guide of ophthalmic drug, Bunkodo Co. Ltd., Tokyo, 387–392, 1994). When 0.5% Compound A is instilled by 50 μl, 1/1000 thereof to be transferred into the anterior chamber is calculated to be $1.5\times10^{-5}$. Therefore, these test results are considered to show the concentration sufficiently effective in vivo as well.

Experimental Example 4

Effect on Normal Intraocular Pressure of White Rabbits

Test Drug

Compound A (+)-trans-4-(1-aminoethyl)-1-(4-pyridylcarbamoyl)cyclohexane 2HCl $1H_2O$ Compound B (+)-trans-N-(1H-pyrrolo[2,3-b]pyridin-4-yl)-4-(1-aminoethyl)cyclohexanecarboxamide 2HCl $6/5H_2O$ Compound C (R)-(+)-N-(4-pyridyl)-4-(1-aminoethyl)benzamide 2HCl)

Compound D (R)-(+)-N-(1H-pyrrolo[2,3-b]pyridin-4-yl)-4-(1-aminoethyl)benzamide 2HCl $1H_2O$ In this experiment, 0.1% eye drop and 0.03% eye drop containing Compound A (each prepared in Example 2 and Example 3), 0.03% eye drop containing Compound B (prepared in Example 4), 0.1% eye drop and 0.03% eye drop containing Compound C (each prepared in Example 5 and Example 6) and 0.03% eye drop containing Compound D (prepared in Example 7) were used.

Experiment Method

Japanese white rabbits (body weight about 2 kg) purchased from Japan Laboratory Animals, INC. were used. These animals were bred in a breeding chamber set to temperature 23±3° C., humidity 55±10% and fed on limited amount of 100 g a day of a solid feed (Labo R Stock, Nihon-Nosan Kogyo K. K.). They were allowed free access to tap water. The rabbits were placed in a holding box for 5 hr a day for acclimation from 2 days prior to the test. The rabbits that showed steady intraocular pressure as measured by a tonometer [pneumatonograph (manufactured by Alcon Lab. Inc.)] were selected and used for the test. After measurement of the initial value of the intraocular pressure, various eye drops (20 μl) were instilled into one eye, and a base, which was one of various eye drops except the test drug, was instilled into the other eye in the same manner and taken as the control eye. The intraocular pressure was measured with time at 30, 60, 90, 120, 150 and 180 min after instillation and thereafter at one hour intervals until the intraocular pressure returned to the initial value, and the duration of the effect was examined.

Experiment Result

Figure 4:
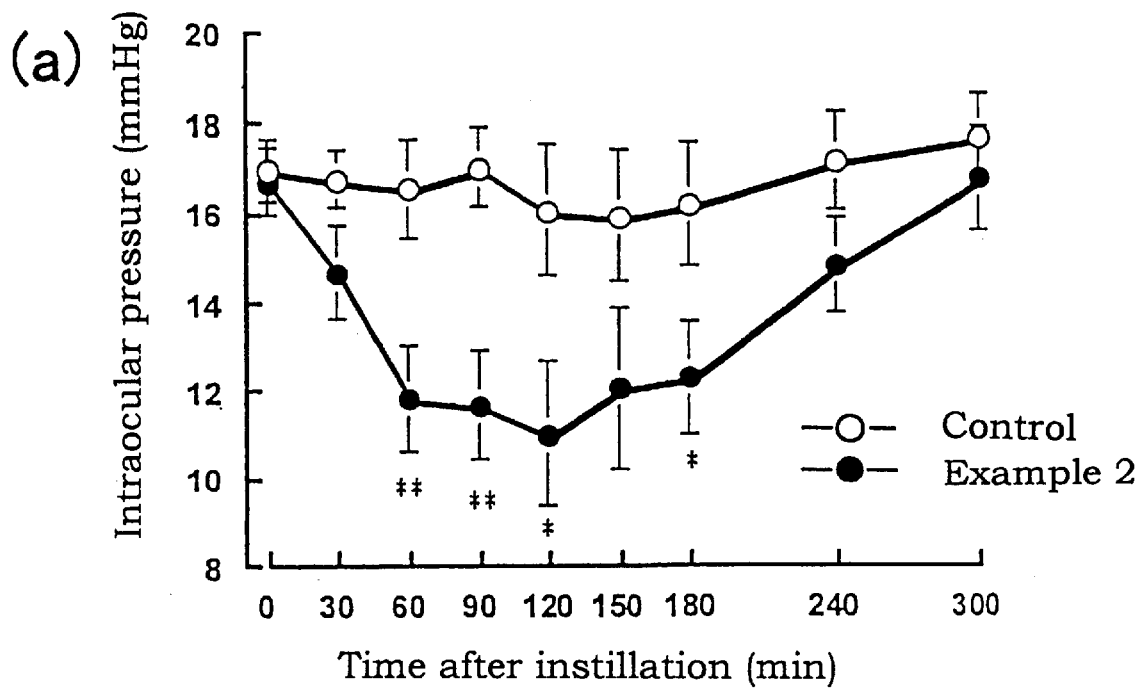
FIG. 4 is a graph showing the effect of the eye drops of Example 2 [0.1% compound A] (a) and Example 5 [0.1% compound C] (b) on the normal intraocular pressure, wherein the ordinate shows intraocular pressure, the abscissa shows time after instillation, ● shows the eye instilled with the eye drop and ○ shows control eye (n=6, *p<0.05, **p<0.01 Student's t-test).
Figure 4:
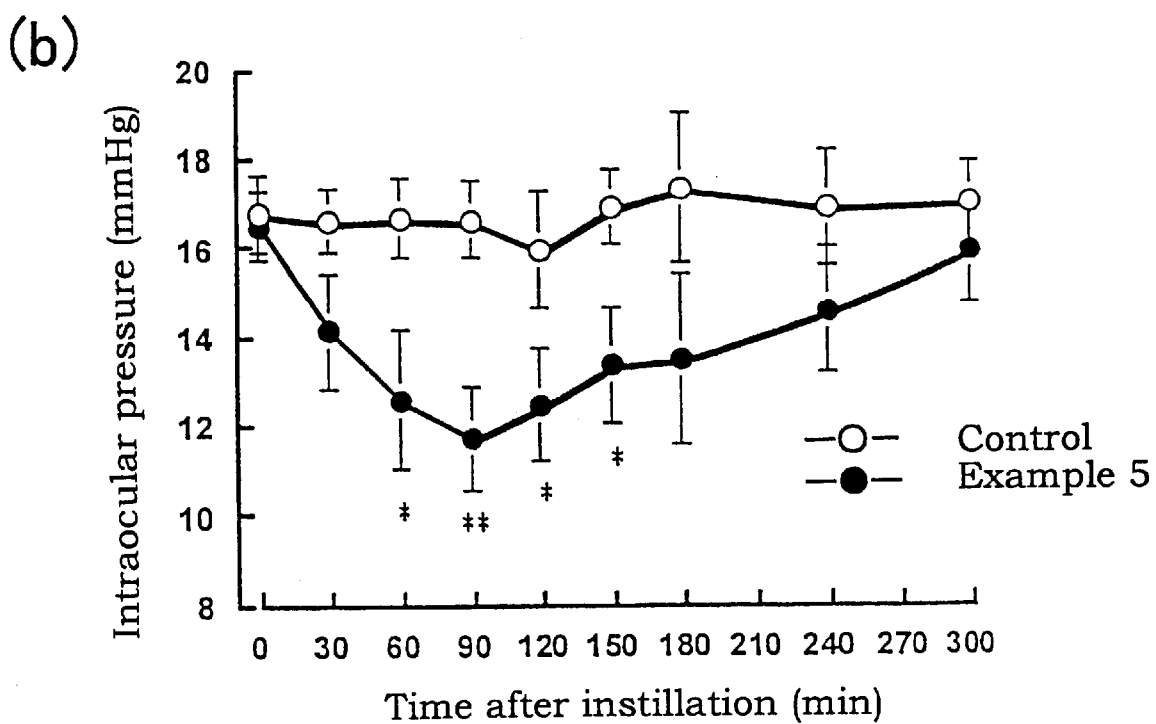
Figure 5:
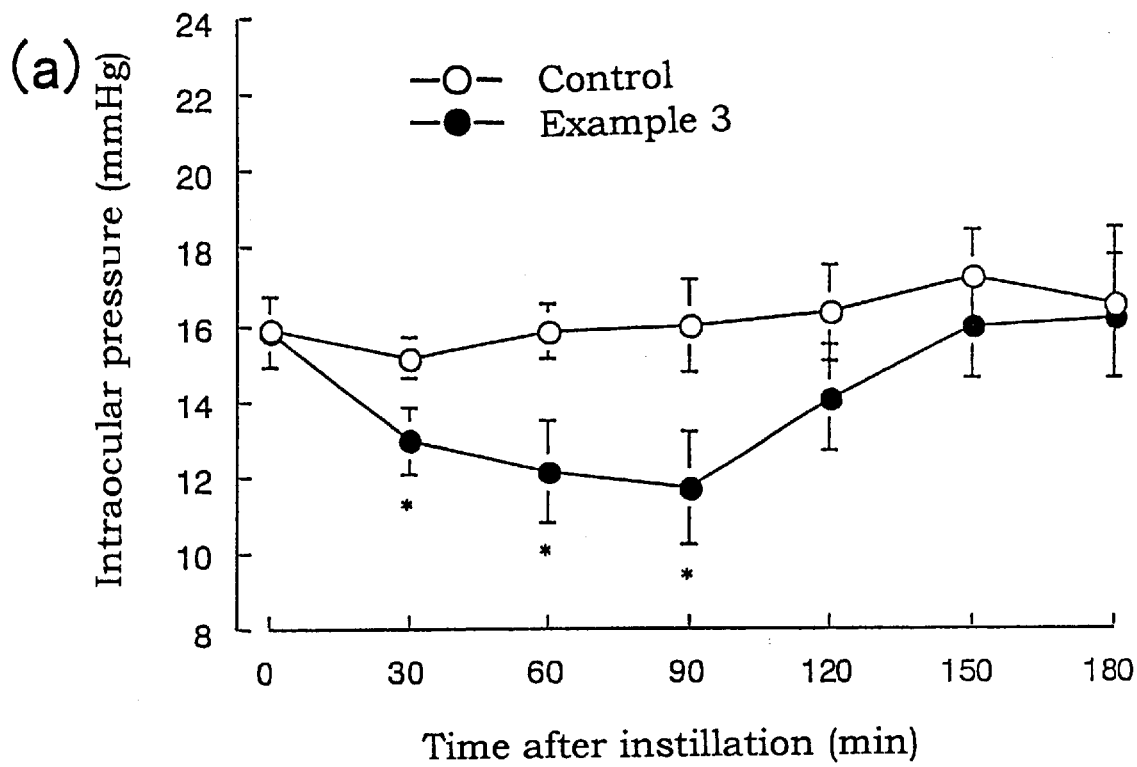
FIG. 5 is a graph showing the effect of the eye drops of Example 3 [0.03% compound A] (a) and Example 4 [0.03% compound B] (b) on the normal intraocular pressure, wherein the ordinate shows intraocular pressure, the abscissa shows time after instillation, ● shows the eye instilled with the eye drop and ○ shows control eye (n=6, *p<0.05 Student's t-test).
Figure 5:
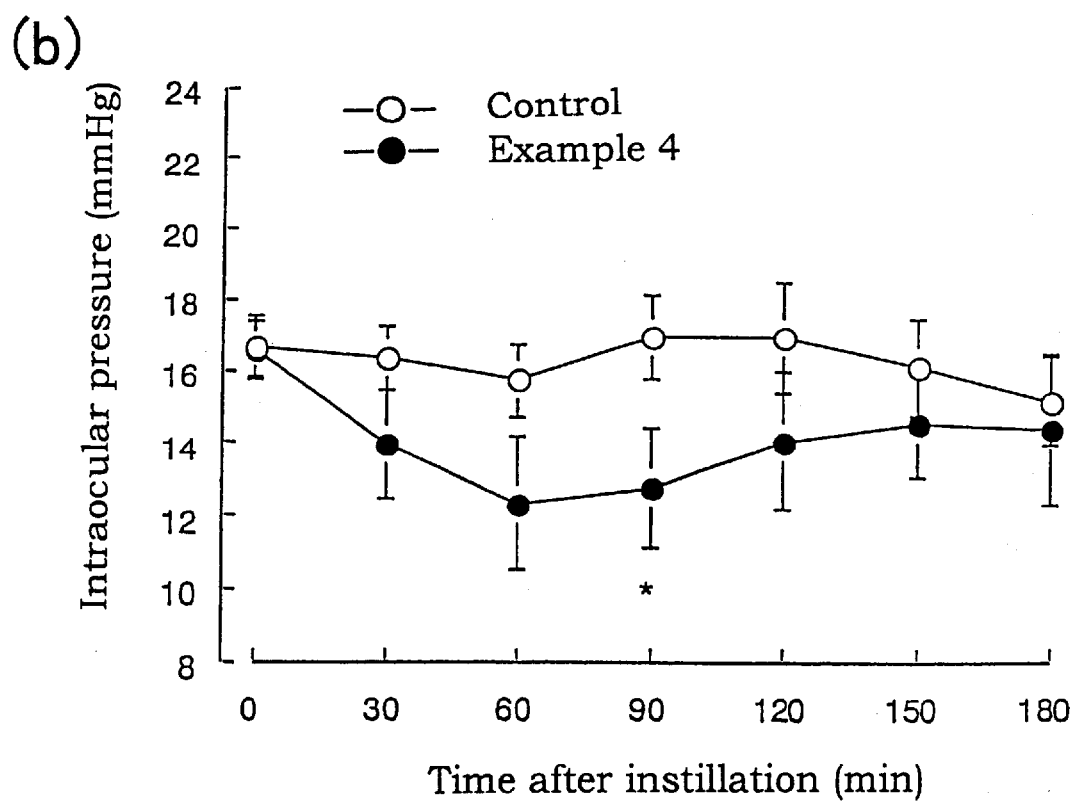
Figure 6:
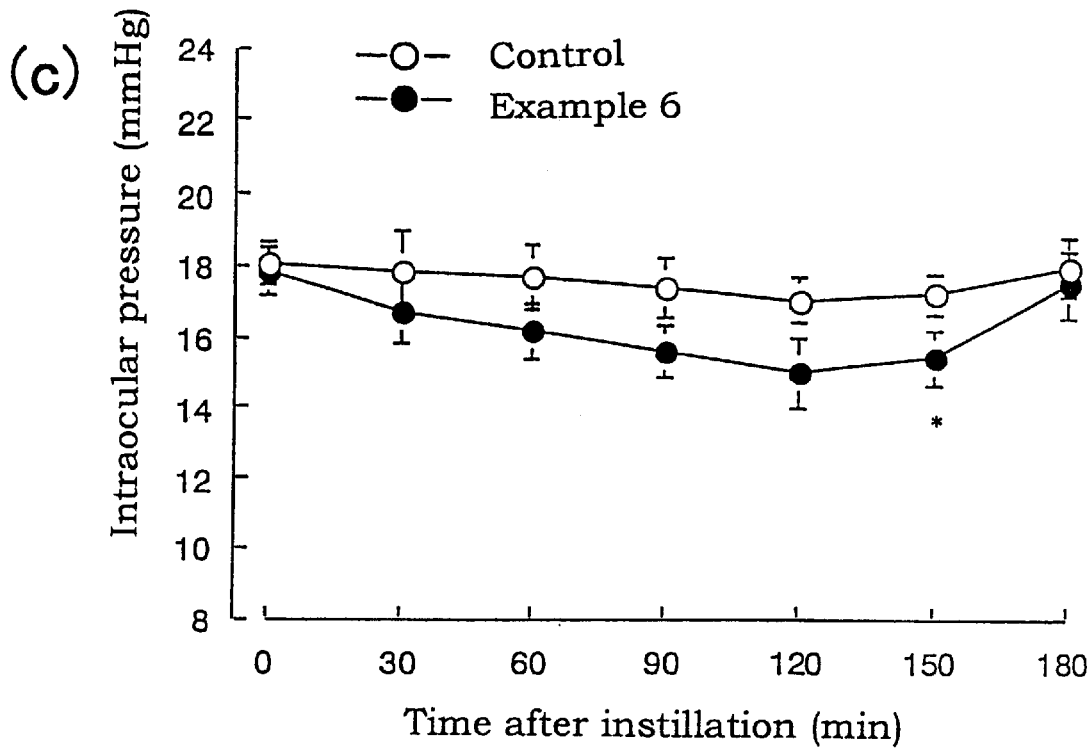
FIG. 6 is a graph showing the effect of the eye drops of Example 6 [0.03% compound C] (c) and Example 7 [0.03% compound D] (d) on the normal intraocular pressure, wherein the ordinate shows intraocular pressure, the abscissa shows time after instillation, ● shows the eye instilled with the eye drop and ○ shows control eye (n=6, *p<0.05, p<0.01, *p<0.001 Student's t-test).
Figure 6:
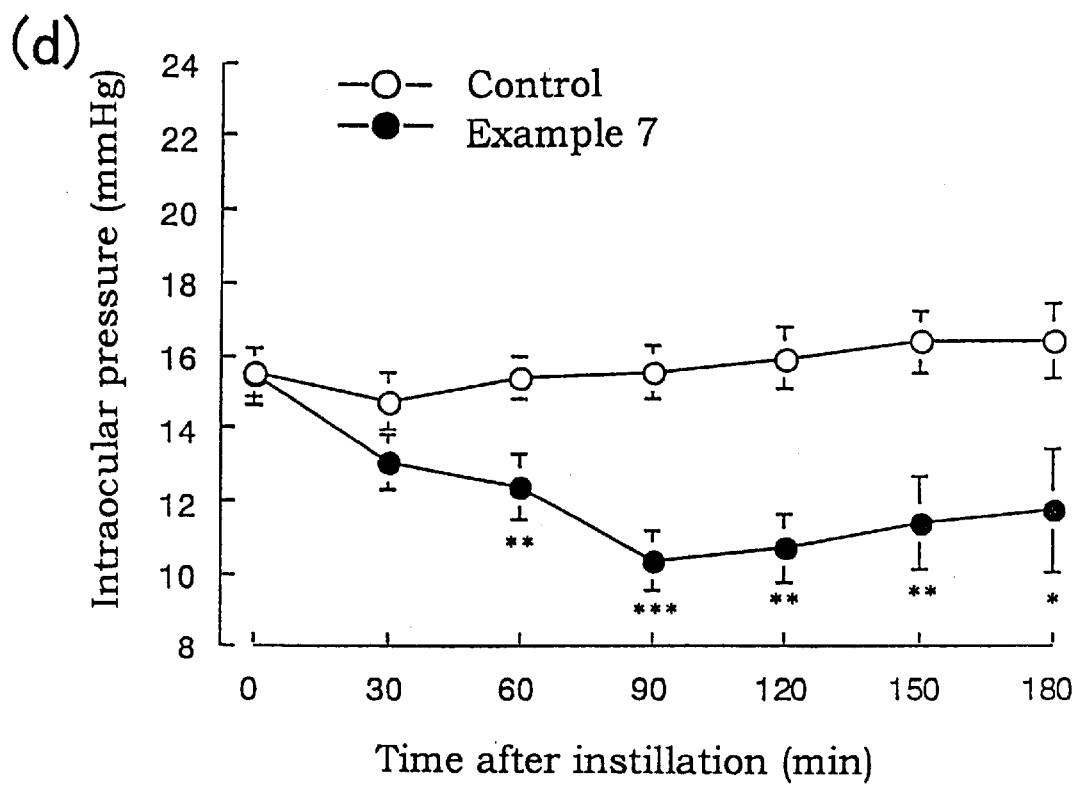

The effects of eye drops containing each test drug at a concentration of 0.1% on the normal intraocular pressure are shown in FIG. 4 (Examples 2, 5). The effects of eye drops containing each test drug at a concentration of 0.03% on the normal intraocular pressure are shown in FIG. 5 (Examples 3, 4) and FIG. 6 (Examples 6, 7). In every case, a significant intraocular pressure lowering effect was found. In particular, Compound A (Examples 2, 3) showed an intraocular pressure lowering effect in early stages after instillation and Compound D (Example 7) showed a marked and long lasting intraocular pressure lowering effect.

Experimental Example 5

Effect on of Blood Flow of Normal Optic Disc of White Rabbits

Test Drug

Compound A (+)-trans-4-(1-aminoethyl)-1-(4-pyridylcarbamoyl)cyclohexane 2HCl 1H$_2$O Compound C (R)-(+)-N-(4-pyridyl)-4-(1-aminoethyl) benzamide 2HCl In this experiment, 0.1% eye drop containing Compound A (prepared in Example 2) and 0.1% eye drop containing Compound C (prepared in Example 5) were used.

Experiment Method

Japanese white rabbits (body weight about 2 kg) purchased from Japan Laboratory Animals, INC. were used. These animals were bred in a breeding chamber set to temperature 23±3° C., humidity 55±10% and fed on limited amount of 100 g a day of a solid feed (Labo R Stock, Nihon-Nosan Kogyo K. K.). They were allowed free access to tap water. In the same manner as in Example 4, each test drug was administered. Using laser speckle microcirculation analyzer, the blood flow of optic disc was measured at 30, 60, 90, 120, 150 and 180 min after instillation and thereafter at one hour intervals till 300 min after the instillation.

Experiment Result

Figure 7:
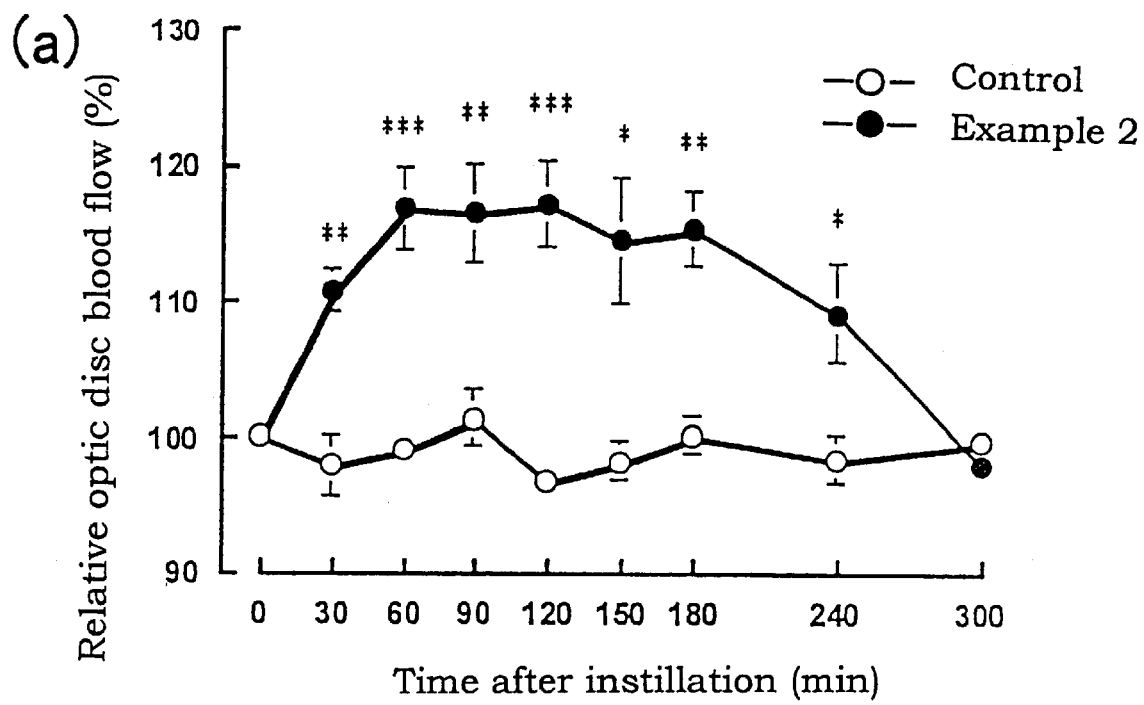
FIG. 7 is a graph showing the effect of the eye drops of Example 2 [0.1% compound A] (a) and Example 5 [0.1% compound C] (b) on the optic disc blood flow kinetic, wherein the ordinate shows relative optic disc blood flow, the abscissa shows time after instillation, ● shows the eye instilled with the eye drop and ○ shows control eye (n=6, *p<0.05, p<0.01, *p<0.001 paired t-test).
Figure 7:
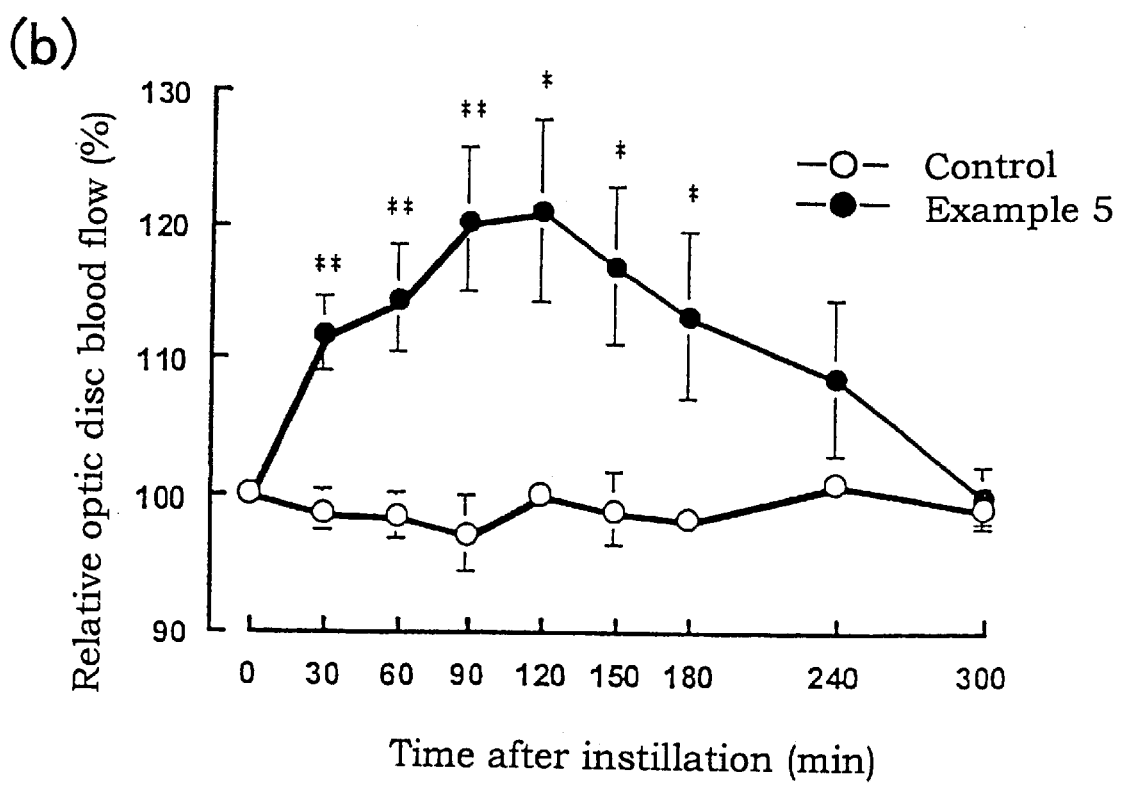

The results are shown in FIG. 7. In every case, a significant blood flow increasing action was observed from 30 min after instillation. In particular, when Compound A (Example 2) was instilled, the effect was more long-lasting.

In consideration of the results of Experimental Example 2, this optic disc blood flow increasing action was considered to be attributable to vasodilation caused by dephosphorylation of vascular smooth muscle myosin light chain due to the activation of myosin phosphatase by a compound having a Rho kinase inhibitory activity (Masayoshi Uehata, et al., Nature 389, 990–994, 1997) and the accompanying increase in ophthalmic perfusion pressure (blood pressure—intraocular pressure).

Experimental Example 6

Ophthalmic Disorder Caused by 8-Time-a-Day Instillation to White Rabbits

Test Drug

Compound A (+)-trans-4-(1-aminoethyl)-1-(4-pyridylcarbamoyl)cyclohexane 2HCl 1H$_2$O Compound C (R)-(+)-N-(4-pyridyl)-4-(1-aminoethyl) benzamide 2HCl The test drugs, Compound A and Compound C, were each dissolved in the following base at a concentration of 0.125, 0.25, 0.5 and 1.0% and adjusted to pH 7 for use in this experiment.

| Formulation of base | |
|---|---|
| Sodium dihydrogenphosphate 2 hydrate | 0.1 g |
| Sodium chloride | 0.9 g |
| Sodium hydroxide | appropriate amount |
| distilled water for injection | appropriate amount |
| Total amount | 100 ml |

Experiment Method

Japanese white rabbits (body weight about 2 kg) purchased from Japan Laboratory Animals, INC. were used. These animals were bred in a breeding chamber set to temperature 23±3° C., humidity 55±10% and fed on limited amount of 100 g a day of a solid feed (Labo R Stock, Nihon-Nosan Kogyo K. K.). They were allowed free access to tap water. Instillation: Using amicropipet, each test drug (100 μl) was instilled into the right eye of each animal 8 times at one hour intervals. Into the left eye was instilled a base in the same manner. Observation: anterior segment of the eye was macroscopically observed before instillation and 30 min after 2nd, 4th, 6th and 8th administrations, according to the macroscopic criteria for ocular lesions as shown in Table 1 (Naruyuki Fukui, Fumihiko Ikemoto, *Gendai no Rinshou* 4, 277–289, 1970). In addition, corneal staining spot was observed before instillation and after 8th administration.

The results of macroscopic observation of the anterior segment of the eye upon administration of Compound A are shown in Table 2 and the results of macroscopic observation of the anterior segment of the eye upon administration of Compound C are shown in Table 3.

TABLE 1

| Macroscopic criteria for ocular lesions in rabbits | |
|---|---|
| Cornea | |
| A. Degree of opacity | |
| No opacity (normal) | 0 |
| Scattered of diffuse areas, details of iris clearly visible | 1 |
| Easily discernible translucent areas, details of iris slightly obscured | 2 |

TABLE 1-continued

Macroscopic criteria for ocular lesions in rabbits

| | |
|---|---|
| Opalescent areas, no details of iris visible, size of pupil barely discernible | 3 |
| Opaque, iris invisible | 4 |

B. Area of opacity

| | |
|---|---|
| One quarter (or less) but not zero | 1 |
| Greater than one quarter but less than half | 2 |
| Greater than half but less than three quarters | 3 |
| Greater than three quarters, up to whole area | 4 |

Iris

Values

| | |
|---|---|
| Normal | 0 |
| Folds above normal congestion, swelling circumcorneal injection (any or all of these or any combination), iris reacts to light (sluggish reaction is positive) | 1 |
| No reaction to light, hemorrhage, gross destruction (any or all or these) | 2 |

Conjunctiva

A. Redness of palpebral conjunctiva

| | |
|---|---|
| No injection | 0 |
| Mucosa tinged very slightly with red, a slight vasodilation in the palpebral edge | 0.5 |
| Obvious injection above normal, mucosa tinged more definitely with red, prominent swelling | 1 |
| Mucosa tinged very markedly with red, slightly indistinct peripheral vessels | 2 |
| Diffuse beefy red (more severe than 2) | 3 |

B) Edema of palpebral conjunctiva

| | |
|---|---|
| No swelling | 0 |
| Slight edematous tendency | 0.5 |
| Swelling above normal | 1 |
| Obvious swelling with partial eversion of lids | 2 |
| Swelling with lids about half closed | 3 |
| Swelling with lids about half closed to completely closed | 4 |

C) Redness of bulbar conjunctiva

| | |
|---|---|
| No injection | 0 |
| Slight vasodilatation of circumcorneal vessels | 0.5 |
| More prominent vasodilation | 1 |
| Marked vasodilation of vessels coursing toward the palpebral edge or the vessels tinged markedly red | 2 |

D. Nictitating membrane

| | |
|---|---|
| No injection | 0 |
| Tendency toward vasodilation and edema | 0.5 |
| More prominent vasodilation, the palpebral edge tinged with red | 1 |
| Very marked vasodilation, the whole nictitating membrane tinged with red | 2 |

TABLE 1-continued

Macroscopic criteria for ocular lesions in rabbits

E) Discharge

| | |
|---|---|
| No discharge | 0 |
| Any amount different from normal (does not include small amounts observed in inner canthus) | 1 |
| Discharge with moistening of the lids and hair just adjacent to lids | 2 |
| Discharge with moistening of the lids and hair, and considerable are around the eye | 3 |

TABLE 2

Scores of ocular lesions in rabbits administered with compound A (mean of three eyes)

| Item for scoring ocular lesions | | Before | 2nd | 4th | 6th | 8th |
|---|---|---|---|---|---|---|
| 0.125% | | | | | | |
| Cornea | Degree | 0 | 0 | 0 | 0 | 0 |
| | Area | 0 | 0 | 0 | 0 | 0 |
| Iris | Values | 0 | 0 | 0 | 0 | 0 |
| Conjunctiva | Palpebral redness | 0 | 0.17 | 0 | 0.33 | 0.33 |
| | Palpebral edema | 0 | 0 | 0 | 0.33 | 0.50 |
| | Bulbar redness | 0 | 0.33 | 0.33 | 0.33 | 0.33 |
| | Nictitating membrane | 0 | 0 | 0 | 0 | 0.17 |
| | Discharge | 0 | 0 | 0.17 | 0.50 | 0 |
| Total score | | 0 | 0.50 | 0.50 | 1.99 | 1.33 |
| 0.25% | | | | | | |
| Cornea | Degree | 0 | 0 | 0 | 0 | 0 |
| | Area | 0 | 0 | 0 | 0 | 0 |
| Iris | Values | 0 | 0 | 0 | 0 | 0 |
| Conjunctiva | Palpebral redness | 0 | 0.17 | 0 | 0.33 | 0.33 |
| | Palpebral edema | 0 | 0 | 0 | 0.17 | 0 |
| | Bulbar redness | 0 | 0.50 | 0.50 | 0.50 | 0.83 |
| | Nictitating membrane | 0 | 0.17 | 0.50 | 0.50 | 0.50 |
| | Discharge | 0 | 0 | 0.17 | 0.50 | 0 |
| Total score | | 0 | 0.84 | 1.00 | 1.50 | 1.66 |
| 0.5% | | | | | | |
| Cornea | Degree | 0 | 0 | 0 | 0 | 0 |
| | Area | 0 | 0 | 0 | 0 | 0 |
| Iris | Values | 0 | 0 | 0 | 0 | 0 |
| Conjunctiva | Palpebral redness | 0 | 0.17 | 0.17 | 0.67 | 0.67 |
| | Palpebral edema | 0 | 0.17 | 0.17 | 0.83 | 0.67 |
| | Bulbar redness | 0.17 | 0.50 | 0.50 | 0.50 | 0.83 |
| | Nictitating membrane | 0 | 0 | 0.33 | 0.50 | 0.67 |
| | Discharge | 0 | 0 | 0.33 | 2.67 | 1.17 |
| Total score | | 0.17 | 0.49 | 1.50 | 5.17 | 4.01 |
| 1.0% | | | | | | |
| Cornea | Degree | 0 | 0 | 0 | 0 | 0 |
| | Area | 0 | 0 | 0 | 0 | 0 |
| Iris | Values | 0 | 0 | 0 | 0 | 0 |
| Conjunctiva | Palpebral redness | 0.17 | 0.50 | 0.50 | 0.83 | 2.17 |
| | Palpebral edema | 0 | 0.67 | 0.67 | 1.33 | 3.00 |
| | Bulbar redness | 0 | 0.50 | 0.50 | 1.17 | 1.50 |

TABLE 2-continued

Scores of ocular lesions in rabbits administered with compound A (mean of three eyes)

| Item for scoring ocular lesions | Instillation | | | | |
|---|---|---|---|---|---|
| | Before | 2nd | 4th | 6th | 8th |
| Nictitating membrane | 0 | 0.17 | 0.50 | 0.67 | 1.67 |
| Discharge | 0 | 0.33 | 0.67 | 1.67 | 2.33 |
| Total score | 0.17 | 2.17 | 2.84 | 5.67 | 10.67 |

TABLE 3

Scores of ocular lesions in rabbits administered with compound C (mean of three eyes)

| Item for scoring ocular lesions | | Instillation | | | | |
|---|---|---|---|---|---|---|
| | | Before | 2nd | 4th | 6th | 8th |
| 0.125% | | | | | | |
| Cornea | Degree | 0 | 0 | 0 | 0 | 0 |
| | Area | 0 | 0 | 0 | 0 | 0 |
| Iris | Values | 0 | 0 | 0 | 0 | 0 |
| Conjunc-tiva | Palpebral redness | 0 | 0 | 0 | 0.17 | 0.33 |
| | Palpebral edema | 0 | 0 | 0 | 0.17 | 0.33 |
| | Bulbar redness | 0 | 0 | 0.50 | 0.17 | 0.50 |
| | Nictitating membrane | 0 | 0 | 0.33 | 0.33 | 0.50 |
| | Discharge | 0 | 0 | 0.17 | 0.50 | 0 |
| Total score | | 0 | 0 | 0.83 | 0.84 | 1.66 |
| 0.25% | | | | | | |
| Cornea | Degree | 0 | 0 | 0 | 0 | 0 |
| | Area | 0 | 0 | 0 | 0 | 0 |
| Iris | Values | 0 | 0 | 0 | 0 | 0 |
| Conjunc-tiva | Palpebral redness | 0 | 0 | 0.33 | 0.33 | 0 |
| | Palpebral edema | 0 | 0 | 0 | 0.17 | 0 |
| | Bulbar redness | 0 | 0.33 | 0.33 | 0.50 | 0.67 |
| | Nictitating membrane | 0 | 0.33 | 0.50 | 0.33 | 1.33 |
| | Discharge | 0 | 0 | 0 | 0.67 | 1.00 |
| Total score | | 0 | 0.66 | 1.50 | 2.83 | 3.00 |
| 0.5% | | | | | | |
| Cornea | Degree | 0 | 0 | 0 | 0 | 0 |
| | Area | 0 | 0 | 0 | 0 | 0 |
| Iris | Values | 0 | 0 | 0.33 | 0 | 0.67 |
| Conjunc-tiva | Palpebral redness | 0 | 0 | 0.33 | 0.33 | 2.00 |
| | Palpebral edema | 0 | 0 | 0.33 | 0.33 | 2.83 |
| | Bulbar redness | 0 | 0.50 | 0.50 | 0.67 | 1.00 |
| | Nictitating membrane | 0 | 0.50 | 0.33 | 1.00 | 1.00 |
| | Discharge | 0 | 0 | 0.17 | 1.00 | 2.00 |
| Total score | | 0 | 1.00 | 1.99 | 3.83 | 9.50 |
| 1.0% | | | | | | |
| Cornea | Degree | 0 | 0 | 0 | 0 | 0 |
| | Area | 0 | 0 | 0 | 0 | 0 |
| Iris | Values | 0 | 0 | 0.67 | 1.00 | 1.00 |
| Conjunc-tiva | Palpebral redness | 0 | 0.17 | 0.50 | 0.50 | 2.33 |
| | Palpebral edema | 0 | 0 | 0.17 | 0.50 | 3.33 |
| | Bulbar redness | 0 | 0.50 | 0.50 | 0.67 | 2.00 |
| | Nictitating membrane | 0 | 0.50 | 0.50 | 0.83 | 1.67 |
| | Discharge | 0 | 0 | 0 | 0.33 | 2.33 |
| Total score | | 0 | 1.17 | 2.34 | 3.83 | 12.66 |

According to the observation of corneal staining spot, the administration of Compound A at any concentration did not lead to abnormalities. In contrast, when Compound C was administered, 0.25% instillation caused abnormality in two eyes, 0.5 and 1.0% instillations caused abnormality in all eyes at corneal epithelium. However, 0.125% instillation did not cause particular abnormality.

INDUSTRIAL APPLICABILITY

In the agent for the prophylaxis and treatment of glaucoma of the present invention, since a compound having a Rho kinase inhibitory activity shows an intraocular pressure lowering effect, an optic disc blood flow improving effect and an aqueous outflow promoting effect, the agent is useful for the prophylaxis and treatment of various types of glaucoma, such as primary open angle glaucoma, normal pressure glaucoma, hypersecretion glaucoma, ocular hypertension, acute angle closure glaucoma, chronic angle closer glaucoma, plateau iris syndrome, combined-mechanism glaucoma, steroid glaucoma, capsular glaucoma, pigmentary glaucoma, secondary glaucoma associated with amyloidosis, neovascular glaucoma, malignant glaucoma and the like.

Inasmuch as the compound having a Rho kinase inhibitory activity inhibits contraction of ciliary muscle, it is useful as an agent for the prophylaxis and treatment of asthenopia and pseudomyopia and the like caused by sustained abnormal tension of ciliary muscle.

This application is based on a patent application Nos. 247762/1998 and 122960/1999 filed in Japan, the content of which is hereby incorporated by reference.

What is claimed is:

1. A method for treating asthenopia, which comprises administering an effective amount of a compound having a Rho kinase inhibitory activity to a patient having asthenopia.

2. A methods for treating pseudomyopia, which comprises administering an effective amount of a compound having a Rho kinase inhibitory activity to a patient having asthenopia.

3. The method of any of claims 1 to 2, wherein the compound having a Rho kinase inhibitory activity is an amide compound of the following formula (I):

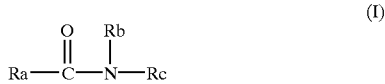

(I)

wherein

Ra is a group of the formula

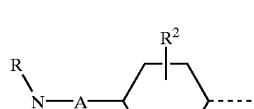

(a)

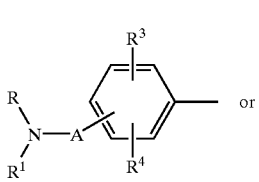

(b)

or

-continued

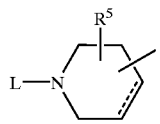
(c)

in the formulas (a) and (b),

R is hydrogen, alkyl, or cycloalkyl, cycloalkylalkyl, phenyl or aralkyl, which optionally has a substituent on the ring, or a group of the formula

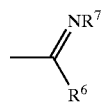
(d)

wherein $R^6$ is hydrogen, alkyl or formula —$NR^8R^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally having, in the ring, oxygen atom, sulfur atom or optionally substituted nitrogen atom, $R^1$ is hydrogen, alkyl, or cycloalkyl, cycloalkylalkyl, phenyl or aralkyl, which optionally has a substituent on the ring, or R and $R^1$ in combination form, together with the adjacent nitrogen atom, a group forming a heterocycle optionally having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, alkylcarbamoyl or azide, and A is a group of the formula

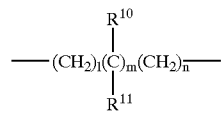
(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, in the formula (c), L is hydrogen, alkyl, aminoalkyl, mono- or dialkylaminoalkyl, tetrahydrofurfuryl, carbamoylalkyl, phthalimidoalkyl, amidino or a group of the formula

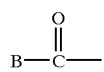
(f)

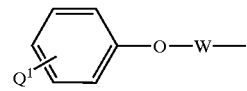
(g)

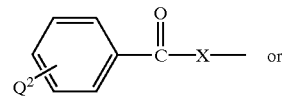
(h)

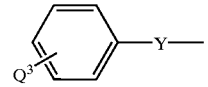
(i)

wherein B is hydrogen, alkyl, alkoxy, aralkyl, aralkyloxy, aminoalkyl, hydroxyalkyl, alkanoyloxyalkyl, alkoxycarbonylalkyl, α-aminobenzyl, furyl, pyridyl, phenyl, phenylamino, styryl or imidazopyridyl, $Q^1$ is hydrogen, halogen, hydroxy, aralkyloxy or thienylmethyl, W is alkylene, $Q^2$ is hydrogen, halogen, hydroxy or aralkyloxy, X is alkylene, $Q^3$ is hydrogen, halogen, hydroxy, alkoxy, nitro, amino, 2,3-dihydrofuryl or 5-methyl-3-oxo-2,3,4,5-tetrahydropyridazin-6-yl;

and Y is a single bond, alkylene or alkenylene, and in the formula (c), a broken line is a single bond or a double bond, and $R^5$ is hydrogen, hydroxy, alkoxy, alkoxycarbonyloxy, alkanoyloxy or aralkyloxycarbonyloxy;

Rb is a hydrogen, an alkyl, an aralkyl, an aminoalkyl or a mono- or dialkylaminoalkyl; and Rc is an optionally substituted heterocycle containing nitrogen, an isomer thereof or a pharmaceutically acceptable acid addition salt thereof.

4. The method of any of one claims 1 or 2, wherein the compound having a Rho kinase inhibitory activity is an amide compound of the following formula (I')

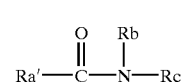
(I')

wherein

Ra' is a group of the formula

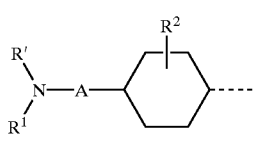
(a')

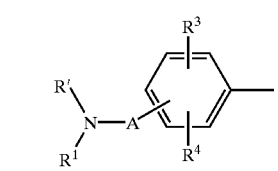
(b')

wherein

R' is hydrogen, alkyl, or cycloalkyl, cycloalkylalkyl, phenyl or aralkyl, which optionally has a substituent on the ring, R¹ is hydrogen, alkyl, or cycloalkyl, cycloalkylalkyl, phenyl or aralkyl, which optionally has a substituent on the ring, or R' and R¹ in combination form, together with the adjacent nitrogen atom, a group forming a heterocycle optionally having, in the ring, oxygen atom, sulfur atom or optionally substituted nitrogen atom, R² is hydrogen or alkyl, R³ and R⁴ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, alkylcarbamoyl or azide, and A is a group of the formula

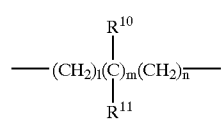  (e)

wherein R¹⁰ and R¹¹ are the same or different and each is hydrogen, alkyl, haloalkyl, aralkyl, hydroxyalkyl, carboxy or alkoxycarbonyl, or R¹⁰ and R¹¹ show a group which forms cycloalkyl in combination and l, m and n are each 0 or an integer of 1–3, Rb is a hydrogen, an alkyl, an aralkyl, an aminoalkyl or a mono- or dialkylaminoalkyl; and Rc is an optionally substituted heterocycle containing nitrogen, an isomer thereof or a pharmaceutically acceptable acid addition salt thereof.

5. The method of claim 4, wherein the compound having a Rho kinase inhibitory activity is (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide, (R)-(+)-N-(1H-pyrrolo[2,3-b]pyridin-4-yl)-4-(1-aminoethyl)benzamide or a pharmaceutically acceptable acid addition salt thereof.

6. The method of claim 4, wherein the compound having a Rho kinase inhibitory activity is administered to a local site on the eye.

7. The method of claim 4, wherein the compound having a Rho kinase inhibitory activity is administered in an eye drop form to the eye.

8. The method of claim 4, wherein the compound having a Rho kinase inhibitory activity is (R)-(+)-N-(1H-pyrrolo[2,3-b]pyridin-4-yl)-4-(1-aminoethyl)benzamide or a pharmaceutically acceptable acid addition salt thereof.

9. The method of claim 8, wherein the compound having a Rho kinase inhibitory activity is a hydrochloric acid salt of (R)-(+)-N-(1H-pyrrolo[2,3-b]pyridin-4-yl)-4-(1-aminoethyl)benzamide.

* * * * *

UNITED STATES PATENT AND TRADEMARK OFFICE
CERTIFICATE OF CORRECTION

PATENT NO.    : 6,649,625 B2
DATED         : November 18, 2003
INVENTOR(S)   : Mitsuyoshi Azuma et al.

It is certified that error appears in the above-identified patent and that said Letters Patent is hereby corrected as shown below:

Column 30,
Line 38, please change "asthenopia" to -- pseudomyopia --.
Line 39, please change "methods" to -- method --.

Signed and Sealed this

Fourth Day of January, 2005

JON W. DUDAS
*Director of the United States Patent and Trademark Office*

UNITED STATES PATENT AND TRADEMARK OFFICE
CERTIFICATE OF CORRECTION

PATENT NO.   : 6,649,625 B2
DATED        : November 18, 2003
INVENTOR(S)  : Mitsuyoshi Azuma et al.

It is certified that error appears in the above-identified patent and that said Letters Patent is hereby corrected as shown below:

Column 30,
Line 39, please change "methods" to -- method --.
Line 41, please change "asthenopia" to -- pseudomyopia --.

This certificate supersedes Certificate of Correction issued January 4, 2005.

Signed and Sealed this

Nineteenth Day of July, 2005

JON W. DUDAS
*Director of the United States Patent and Trademark Office*